United States Patent
Hansson et al.

(10) Patent No.: US 12,161,531 B2
(45) Date of Patent: *Dec. 10, 2024

(54) MEDICAL DRESSING

(71) Applicant: Mölnlycke Health Care AB, Gothenburg (SE)

(72) Inventors: Dennis Hansson, Gunnilse (SE); Karin Glasmästar, Hisings Backa (SE); Anna Grou, Gothenburg (SE); Conny Jakobsson, Lerum (SE); Océane Lançon, Säve (SE)

(73) Assignee: Mölnlycke Health Care AB, Gothenburg (SE)

( * ) Notice: Subject to any disclaimer, the term of this patent is extended or adjusted under 35 U.S.C. 154(b) by 1110 days.

This patent is subject to a terminal disclaimer.

(21) Appl. No.: 16/770,152

(22) PCT Filed: Dec. 12, 2018

(86) PCT No.: PCT/EP2018/084623
§ 371 (c)(1),
(2) Date: Jun. 5, 2020

(87) PCT Pub. No.: WO2019/115643
PCT Pub. Date: Jun. 20, 2019

(65) Prior Publication Data
US 2021/0161724 A1 Jun. 3, 2021

(30) Foreign Application Priority Data

Dec. 15, 2017 (EP) .................................. 17207749
Dec. 15, 2017 (EP) .................................. 17207759

(51) Int. Cl.
*A61F 13/00* (2024.01)
*A61F 5/34* (2006.01)
(Continued)

(52) U.S. Cl.
CPC ............ *A61F 13/0213* (2013.01); *A61F 5/34* (2013.01); *A61F 13/0226* (2013.01);
(Continued)

(58) Field of Classification Search
CPC ............................................ A61F 2013/00089
See application file for complete search history.

(56) References Cited

U.S. PATENT DOCUMENTS

| 4,727,868 A | 3/1988 | Szycher et al. |
| 4,909,244 A | 3/1990 | Quarfoot |

(Continued)

FOREIGN PATENT DOCUMENTS

| CA | 2028528 C | * 12/2001 | ......... A61F 13/0203 |
| CA | 2184443 C | * 5/2007 | ........... A61F 13/023 |

(Continued)

OTHER PUBLICATIONS

CA 2028528 C (Year: 2001).*
(Continued)

*Primary Examiner* — Kim M Lewis
(74) *Attorney, Agent, or Firm* — Ballard Spahr LLP

(57) ABSTRACT

A medical dressing is described for prevention of pressure ulcers. The dressing has a gel pad and an anisotropic layer being stiffer in one layer direction. The dressing reduces the shear and compression forces on the skin and in the underlying the soft tissue layers and prevents the onset of pressure ulcers.

16 Claims, 10 Drawing Sheets

(51) Int. Cl.
  *A61F 13/0203* (2024.01)
  *A61F 13/0246* (2024.01)
  *A61F 13/05* (2024.01)
  *A61L 15/24* (2006.01)
  *A61L 15/26* (2006.01)
  *A61L 15/42* (2006.01)

(52) U.S. Cl.
  CPC .......... *A61F 13/0246* (2013.01); *A61F 13/05* (2024.01); *A61L 15/24* (2013.01); *A61L 15/26* (2013.01); *A61L 15/42* (2013.01); *A61F 2013/00246* (2013.01); *A61F 2013/00404* (2013.01)

(56) References Cited

U.S. PATENT DOCUMENTS

| | | | |
|---|---|---|---|
| 5,056,510 | A | 10/1991 | Gilman et al. |
| 5,056,511 | A | 10/1991 | Ronge et al. |
| 5,056,512 | A | 10/1991 | Bower et al. |
| 5,700,254 | A | 12/1997 | McDowall et al. |
| 5,704,905 | A * | 1/1998 | Jensen ................ A61F 13/0213 602/42 |
| 5,788,684 | A | 8/1998 | Abuto et al. |
| 5,973,221 | A | 10/1999 | Collyer |
| 6,040,493 | A | 3/2000 | Cooke et al. |
| 8,759,454 | B2 | 6/2014 | Kwon et al. |
| 10,080,555 | B2 | 9/2018 | Llinas et al. |
| 10,973,692 | B2 | 4/2021 | Rule et al. |
| 11,890,170 | B2 * | 2/2024 | Rodzewicz ........... A61F 13/069 |
| 2001/0041933 | A1 | 11/2001 | Thoma et al. |
| 2002/0193767 | A1 | 12/2002 | Mavinkurve et al. |
| 2003/0225356 | A1 | 12/2003 | Kulichikhin et al. |
| 2004/0138604 | A1 | 7/2004 | Sigurjonsson et al. |
| 2005/0059918 | A1 | 3/2005 | Sigurjonsson et al. |
| 2008/0039759 | A1 | 2/2008 | Holm et al. |
| 2009/0148394 | A1 | 6/2009 | Munro |
| 2009/0177135 | A1 | 7/2009 | Rogers et al. |
| 2009/0187130 | A1 | 7/2009 | Asmus et al. |
| 2010/0211029 | A1 | 8/2010 | Tsai et al. |
| 2012/0029455 | A1 | 2/2012 | Perez-Foullerat et al. |
| 2013/0053747 | A1 | 2/2013 | Lin |
| 2013/0096478 | A1 | 4/2013 | Cureton |
| 2013/0138068 | A1 | 5/2013 | Hu et al. |
| 2014/0107561 | A1 | 4/2014 | Dorian et al. |
| 2017/0135862 | A1 | 5/2017 | Tuck et al. |
| 2020/0115539 | A1 | 4/2020 | Kudo et al. |
| 2020/0255992 | A1 | 8/2020 | Parsons et al. |
| 2020/0383839 | A1 | 12/2020 | Rodzewicz et al. |

FOREIGN PATENT DOCUMENTS

| | | | |
|---|---|---|---|
| CN | 102209508 A | 10/2011 | |
| EP | 2001424 | 12/2008 | |
| EP | 2829287 A1 * | 1/2015 | ............ A61B 17/08 |
| EP | 3085344 | 10/2016 | |
| EP | 3260098 | 12/2017 | |
| GB | 1049196 | 11/1966 | |
| JP | 2014/168573 | 9/2014 | |
| WO | WO 1996/10972 | 4/1994 | |
| WO | WO 0132121 | 5/2001 | |
| WO | WO 2001/96422 A1 | 12/2001 | |
| WO | WO 2007/113597 | 10/2007 | |
| WO | WO 2008/149107 A1 | 6/2008 | |
| WO | WO2010048078 | 4/2010 | |
| WO | WO 2012/048128 A2 | 4/2012 | |
| WO | WO 2014/058532 | 4/2014 | |
| WO | WO 2016/030047 | 3/2016 | |

OTHER PUBLICATIONS

CA 2184443 C (Year: 2007).*
EP 2829287 A1 (Year: 2015).*
Levy, Ayelet, et al. "The Contribution of a Directional Preference of Stiffness to the Efficacy of Prophylactic Sacral Dressings in Protecting Healthy and Diabetic Tissues from Pressure Injury: Computational Modelling Studies." International Wound Journal, vol. 14, No. 6, 2017, pp. 1370-1377, https://doi.org/10.1111/iwj. 12821.
International Search Report and Written Opinion were mailed on Feb. 28, 2019 by the International Searching Authority for International Application No. PCT/EP2018/084627, filed on Dec. 12, 2018 and published as WO 2019/115645 on Jun. 20, 2019 (Applicant—Mölnlycke Health Care AB) (10 Pages).
European Search Report and Written Opinion were mailed on Feb. 26, 2018 by the European Patent Office for EP Application No. 17207749.7, filed on Dec. 15, 2017 and published as EP 3498241 A1 on Jun. 19, 2019 (Applicant—Mölnlycke Health Care AB) (7 Pages).
European Search Report and Written Opinion were mailed on Apr. 9, 2018 by the European Patent Office for EP Application No. 17207759.6, filed on Dec. 15, 2017 and published as EP 3498244 A1 on Jun. 19, 2019 (Applicant—Mölnlycke Health Care AB) (11 Pages).
International Search Report and Written Opinion were mailed on Mar. 4, 2019 by the International Searching Authority for International Application No. PCT/EP2018/084623, filed on Dec. 12, 2018 and published as WO 2019/115643 on Jun. 20, 2019 (Applicant—Mölnlycke Health Care Ab) (14 Pages).

* cited by examiner

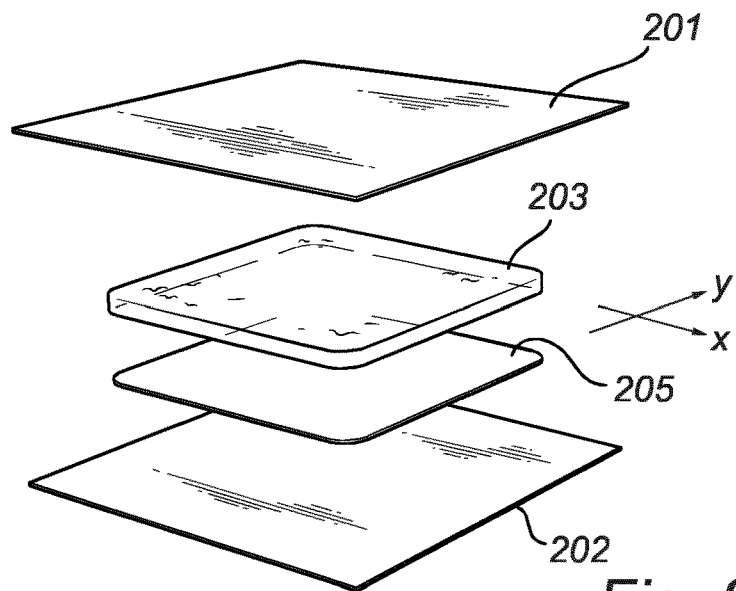
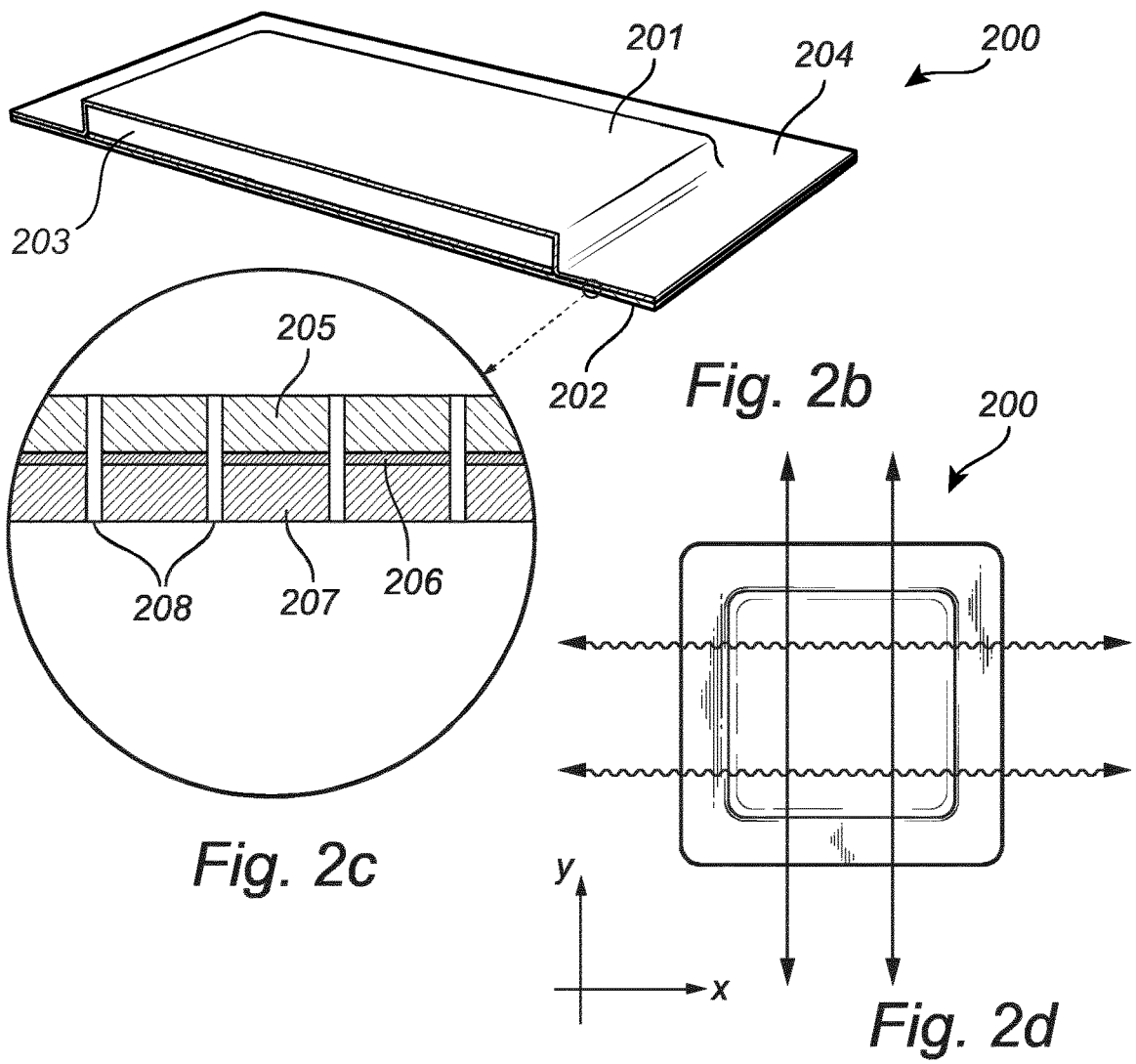
Fig. 2a
Fig. 2b
Fig. 2c
Fig. 2d

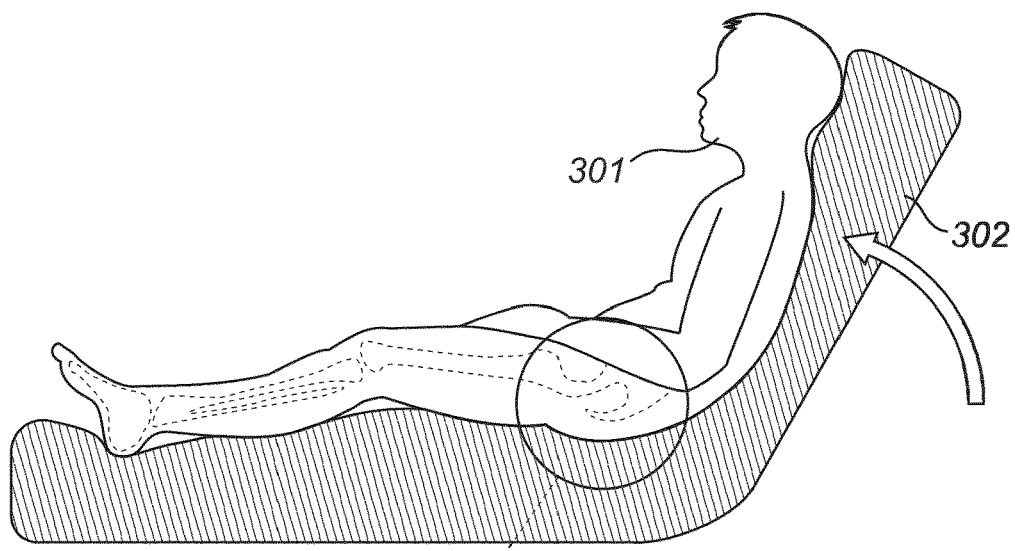
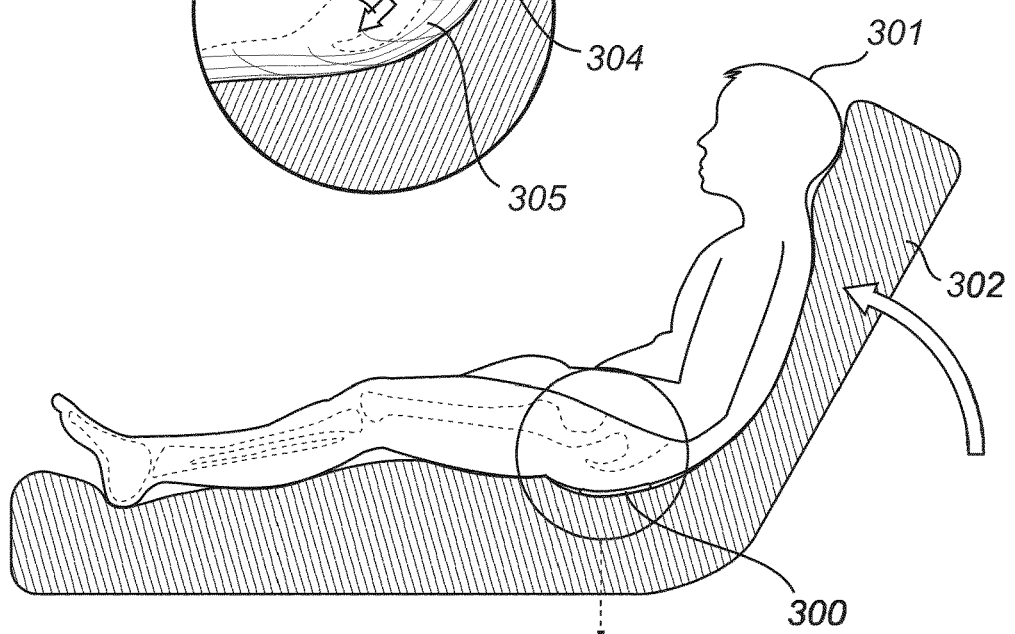
*Fig. 3a*
*Fig. 3b*

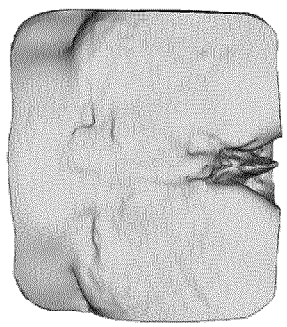
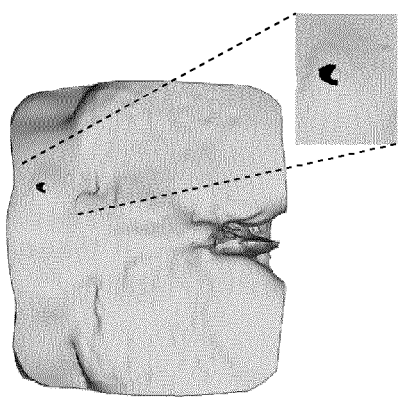
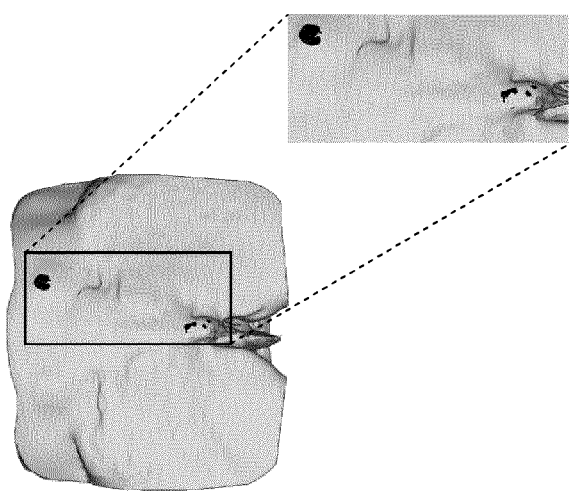
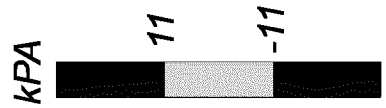
Fig. 7a  Fig. 7b  Fig. 7c

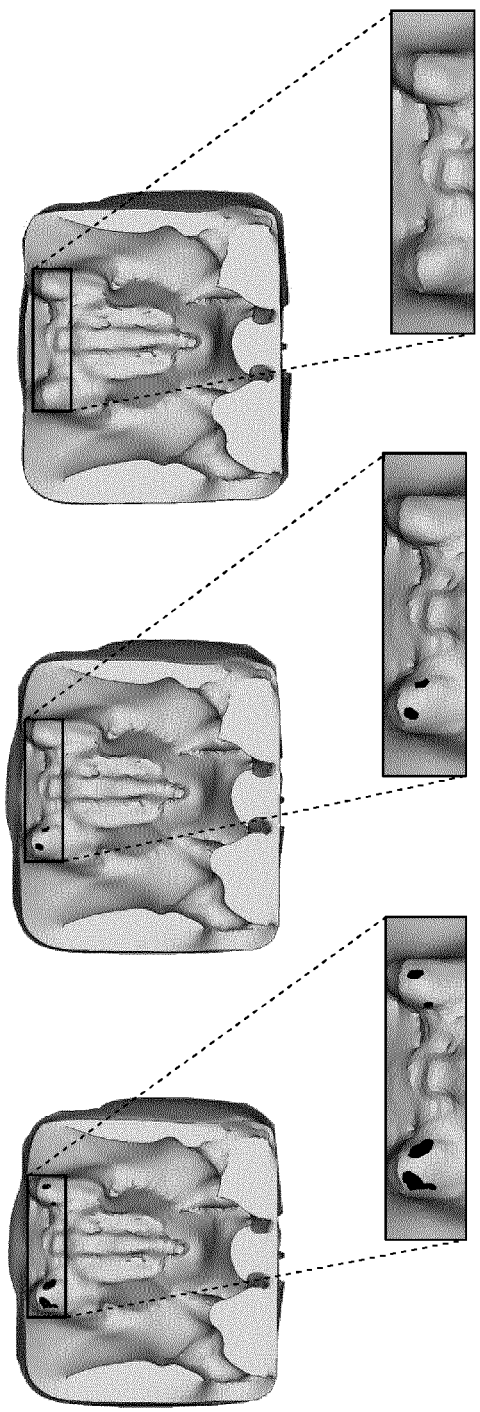
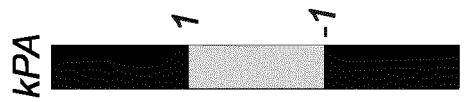
Fig. 8a Fig. 8b Fig. 8c

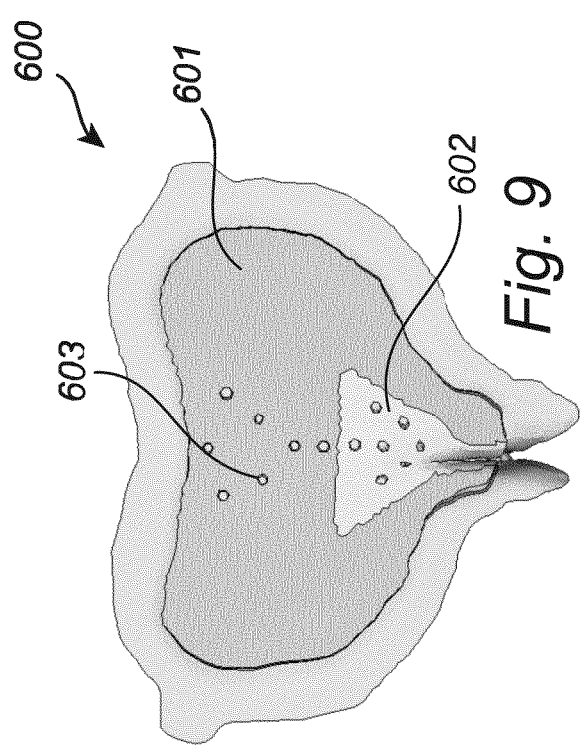
Fig. 9
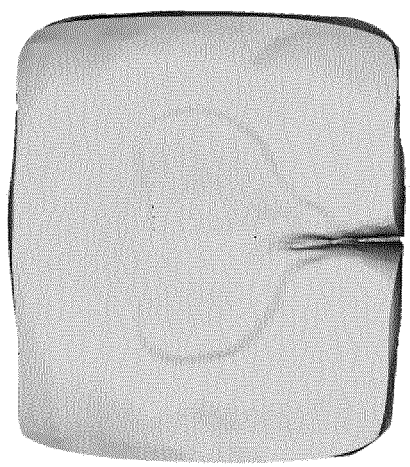
Fig. 10c
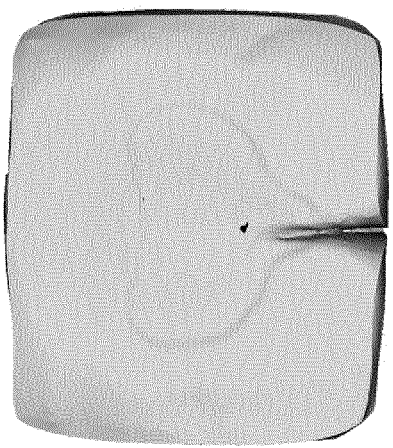
Fig. 10b
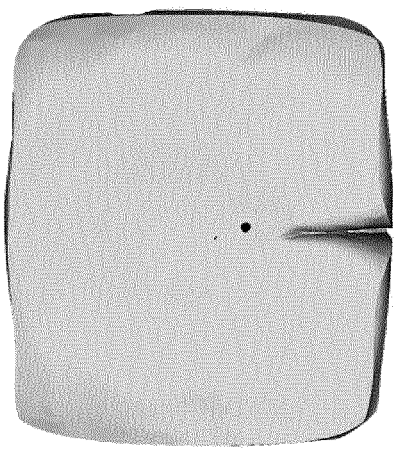
Fig. 10a
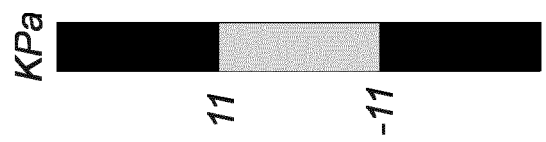

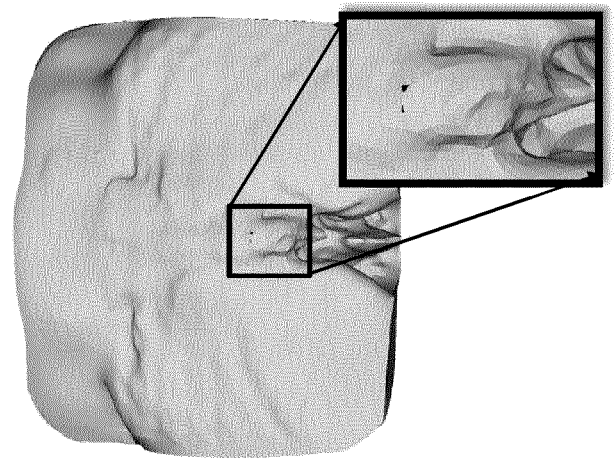
*Fig. 11c*
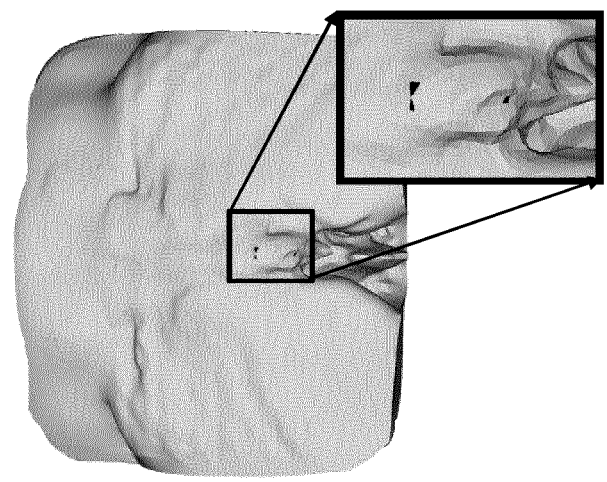
*Fig. 11b*
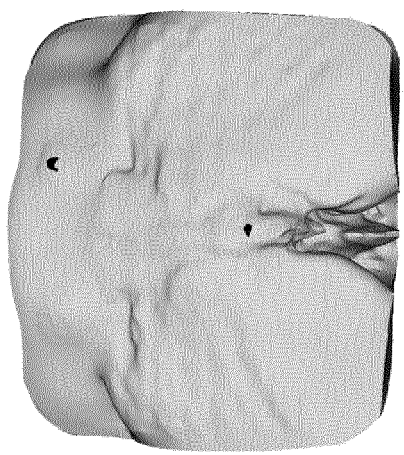
*Fig. 11a*
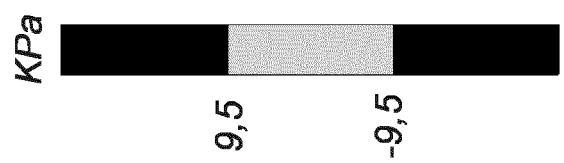

MEDICAL DRESSING

CROSS-REFERENCE TO RELATED APPLICATIONS

This application is a U.S. National Phase Application of International Application No. PCT/EP2018/084623, filed Dec. 12, 2018, which claims priority to European Application Nos. 17207749.7, filed Dec. 15, 2017, and 17207759.6, filed Dec. 15, 2017, each of which are hereby incorporated by reference in their entirety.

TECHNICAL FIELD

The present invention relates to a medical dressing comprising a gel pad and an anisotropic layer. The dressing is suitable for the prevention and/or mitigation of pressure ulcers.

BACKGROUND

A pressure ulcer is a localized injury to the skin and/or underlying tissue over a bony prominence that results from sustained pressure, often in combination with friction and shear. The major factors leading to pressure ulcers or pressure injuries are pressure, shear, friction and unfavourable microclimate. Other factors, intrinsic to patients, may also increase the likelihood of pressure ulcer development, e.g. poor perfusion, reduced sensation and inadequate nutrition. Pressure ulcers often arise among persons being bedridden for various reasons, such as for instance due to long term hospitalization or other causes of immobility. Pressure ulcers also may occur beneath medical devices, such as nasogastric tubes, ventilation masks and tracheostomy tubes, which are applied for diagnostic or therapeutic purposes. The rigid materials used in these devices may abrade the skin and create pressure on the soft tissues.

A pressure ulcer does not always start at the skin surface. What is observed at the skin is often only a small part of the sore, and this may mislead the patient or his/her caregiver to believe that there is only a minor problem.

Pressure ulcers often develop in soft tissue under the skin which covers bony areas of the body (so called "bony prominences"), for example the heels, ankles, the hips or the sacrum. Pressure and shear forces may cause blood vessels to become squeezed between the skin surface and bone. Hence, muscles and tissue under the skin near the bone surface typically suffer the greatest damage. Accordingly, any pressure ulcer as apparent on the skin, regardless of how small, should be regarded as critical because of the probable damage below the skin surface.

A pressure ulcer can be classified into four categories: in the first category, the skin appears pink, reddened or discoloured, and may feel hard and warm to touch. In the second category, the skin breaks open and an ulcer that may look like a blister is formed. In this stage, the skin may be damaged beyond repair or may die. A category three pressure ulcer is an ulcer that extends into the tissue beneath the skin, forming a small crater. In category four, the pressure sore is very deep, reaching into the muscle and bone and causing extensive damage to deeper tissue and tendons. Serious complications, such as infection of the bone or blood may occur if the pressure ulcer progresses.

In some hospitals, caregivers apply wound dressings to areas at risk of developing pressure ulcers, for example in the sacrum, at the heels or under medical devices such as oxygen masks, and feeding, tracheostomy and nasogastric tubes. These dressings used are not primarily designed for prophylactic purposes.

Furthermore, when a dressing has been applied, the skin underneath the dressing must be regularly inspected, typically at least twice a day, to assess the skin status and ensure that there is no sign of damage. This requires the dressing to be peeled back to allow for assessment of the skin. The dressing may need to be opened up and re-applied several times during the day. The adhesive capacity of dressing is thus impaired.

Pressure ulcers are a global problem and the possibility to prevent these is desirable both to reduce human suffering but also to avoid unnecessary costs. The average cost for a category 3 or 4 pressure ulcer is estimated to be from 75000 to 125000 US dollars per patient.

To summarize, there is a need to provide a dressing having an improved prophylactic effect; i.e. a dressing aimed at preventing a pressure ulcer from occurring in the first place and for preventing the progress of an already existing pressure ulcer. Furthermore, there is a need to provide for a proactive and cost-efficient means to minimize the burden for caregivers and staff dealing with pressure ulcers.

SUMMARY

According to at least one aspect of the invention, there is provided a medical dressing comprising a backing layer, a body contact layer and a gel pad arranged between the backing layer and the body contact layer, wherein the backing layer and the body contact layer extend beyond the periphery of the gel pad to define a border portion around the contour of the pad, wherein the dressing further comprises an anisotropic layer having a first (x) direction and a second (y) direction being perpendicular to the first (x) direction, wherein the anisotropic layer is stiffer in the second (y) direction than in first (x) direction.

In embodiments, the body contact layer is an adhesive body contact layer.

The medical dressing is particularly useful for pressure ulcer prevention and/or pressure ulcer mitigation. The inventors have found that the incorporation of a layer having anisotropic stiffness properties into the dressing has a preventative effect on the formation of pressure ulcers. In use, the dressing should be applied such that its second (y) direction corresponds to the direction in which the patient is exposed to most shear forces. For example, when the dressing is applied to the sacral region of a patient, the dressing is stiffer in the direction in which the patient slides in bed. This is normally along the length of the patient. On the other hand, the first (x) direction of the dressing is preferably more stretchable and pliable. This is beneficial since the first (x) direction of the dressing corresponds to the direction by which the patient, wearing such dressing, will be turned and re-positioned by nursing personnel. A bedridden patient at risk of developing pressure ulcers is turned and repositioned at regular intervals. It is therefore advantageous that the dressing conforms to this lateral movement and stays on the skin.

Furthermore, stretchability in the first (x) direction is advantageous since it prevents the skin and underlying tissues from becoming "over constrained" which could otherwise be the case when the dressing is too stiff in both the first and the second directions.

In embodiments, the anisotropic layer is arranged between the gel pad and the backing layer.

In alternative embodiments, the anisotropic layer is arranged between the gel pad and the body contact layer.

Both embodiments are advantageous in terms of minimizing or mitigating harmful shear and compression forces at the skin and in soft tissue layers beneath the dressing.

Pressure ulcer formation in the soft tissue and at the skin is thus prevented and/or mitigated.

The inventors have found that anisotropy in close proximity of the skin improves the prophylactic effect of the dressing.

In exemplary embodiments, the anisotropic layer is an integral part of the body contact layer, i.e. cannot be peeled off said body contact layer during regular use.

In embodiments, the body contact layer may comprise an anisotropic layer and an adhesive layer. Alternatively, the body contact layer may be a laminate comprising the anisotropic layer.

The incorporation of an anisotropic layer into the body contact layer does not only improve the prophylactic effect of the dressing, but also facilitates inspection of the skin. The integrity of the body contact layer, and hence also the border portion of the dressing is improved. A caregiver must regularly inspect the skin beneath the dressing, which requires the dressing to be detached and re-attached several times a day. When the dressing is re-applied to the skin, wrinkles may form in the border portion, which reduces the adhesive capacity of the body contact layer, and hence also the wear time of the dressing. The anisotropic layer increases the rigidity of the border and prevents it from "rolling up" when the dressing is in use, as well preventing wrinkle formation when re-applied.

In embodiments, the anisotropic layer has a tensile force at 15% strain in the second (y) direction of at least 4 N, preferably at least 10 N, and most preferably at least 15 N, as measured by the tensile test described herein.

The structural integrity as well as the prophylactic effect of the dressing is thereby improved. The skin cells and underlying soft tissue cells are protected from becoming extensively damaged since the pressure and shear forces inflicted on a patient laying down on a hospital bed (e.g. a bedridden patient) are reduced. Stiffness in the direction of shear exposure protects the skin cells and deeper tissue layer cells from stretching, and thereby deforming.

In embodiments, the anisotropic layer has a tensile force at 15% strain in the second (y) direction that is at least 6 times higher, preferably at least 10 times higher than in the first (x) direction, as measured by the tensile test described herein.

Accordingly, the stay-on ability of the dressing on the skin is enhanced, and the skin and underlying tissue is prevented from becoming over constrained which could otherwise be the case if the dressing is too stiff in the first (x) direction.

In embodiments, the dressing is substantially transparent.

The gel pad, and, if present, additional components of the dressing is/are preferably transparent. This is to enable visual inspection of the skin underneath the dressing. Although the dressing still needs to be lifted to inspect the skin underneath, the transparency reduces the frequency of detachment and re-application of the dressing which may result in a longer wear time of the dressing. Furthermore, marks can be made on the dressing (or photographs taken) to be able to compare size of redness at the next assessment. The transparency of the dressing allows for the patient to inspect himself or herself and facilitates inspection by caregivers and/or relatives, and the chances of earlier detection of damage are higher.

In embodiments, the gel pad has an opacity of less than 25%, preferably less than 15%, as measured by the opacity test described herein.

This allows for optimal inspection of the skin beneath the dressing, and any discoloration or reddened part of the skin may be detected at an early stage.

In embodiments, the gel has a compressive strength of from 1 to 30 kPa, preferably from 1 to 15 kPa at a strain of 25%, as measured according to the compression test described herein.

The gel is preferably soft and pliable. A too rigid dressing may cause increased stresses in the soft tissue layers, which may increase the risk of developing pressure ulcers In embodiments, the gel has a compressive strength of from 5 to 70 kPa, preferably from 5 to 50 kPa at a strain of 50%, as measured according to the compression test described herein.

This compressive strength is advantageous for the purpose of preventing and/or mitigating pressure ulcers. The soft tissue underneath the dressing is protected from becoming damaged and deformed, and the gel pad may reduce pressure, shear and friction forces occurring at the skin and in the soft tissue layers. The gel dressing of the present invention allows for compression at high loads. The comparatively low compressive strength of the gel at higher strains (50%) prevents deformation (resulting from compression) to be transferred to the underlying skin and soft tissue. Instead deformation due to high load is taking place within the dressing.

The sacral region is an area at particular risk for pressure ulcers. Therefore, in embodiments, the dressing has a shape that conforms with the anatomy of the sacrum.

Hence, the dressing has a lateral (x) extension and a longitudinal (y) extension; the pad being symmetric about a longitudinal center line and the dressing comprising a first lobed portion on one side of the longitudinal center line and a second lobed portion on the other side of the longitudinal center line.

In embodiments, the anisotropic layer is arranged such that the first (x) direction of the anisotropic layer corresponds to the lateral (x) extension of the dressing, and the second (y) direction of the anisotropic layer corresponds to the longitudinal (y) extension of the dressing.

As explained hereinbefore, the dressing protects the skin cells and deeper tissue layer cells from stretching and becoming deformed. The dressing according to the present invention also improves the stay-on ability of the dressing since the dressing is more stretchable in the first (x) direction enabling patient turning and re-positioning without the dressing falling off.

In embodiments, the medical dressing is divided into three separate zones along the longitudinal (y) extension of the dressing: one central zone and two lateral zones, wherein the gel pad comprises a plurality of indentations, at least in the central zone of the dressing.

The central zone of the dressing is the area typically exposed to most stresses, especially in the lower part of the central zone which is arranged to cover the coccyx region of a patient. The indentations allow for a localized softening of the gel pad while preserving the overall properties of the gel dressing. The inventors have found that the skin and the soft tissue underneath is better protected by the provision of indentations in the central zone.

In embodiments, the medical dressing is divided into three separate zones along the longitudinal (y) extension of the dressing: one central zone and two lateral zones, wherein the compressive strength of the gel in the central zone is lower than in the lateral zones.

Accordingly, the dressing may be formed of different regions having different properties; i.e. different compressive strengths. As mentioned, the central zone is typically exposed to the most stresses when the dressing is in use. The inventors have found that this region may be softer, i.e. have a lower compressive strength to prevent the soft tissue cells from becoming deformed and damaged. Accordingly, the central dressing zone may have a compressive strength in the range specified above, and the lateral zones of the dressing may have a higher compressive strength. This may be beneficial to avoid or mitigate flattening of the gel pad in the edges.

The medical dressing may still need to be opened up from time to time. Therefore, to facilitate inspection of the skin, the dressing may comprise at least one gripping tab, wherein the tab preferably is coplanar with and projects outwardly from the periphery of the dressing.

The gripping tab guides the caregiver to lift the dressing, inspect the skin underneath the dressing, and to thereafter re-apply the dressing onto the skin.

In another aspect, the present invention relates to a dressing as described hereinbefore for use in the prevention of pressure ulcers.

Further features of, and advantages with, the present invention will become apparent when studying the appended claims and the following description. The skilled addressee realizes that different features of the present invention may be combined to create embodiments other than those described in the following, without departing from the scope of the present invention.

BRIEF DESCRIPTION OF THE DRAWINGS

FIG. 2a is a split view of a dressing according to one exemplary embodiment of the present invention.

FIG. 2b is a cross-sectional view according to one exemplary embodiment of the present invention.

FIG. 2c is a zoomed-in view of the body contact layer of the dressing illustrated in FIG. 2b.

FIG. 2d illustrates the anisotropic properties of a dressing according to the present invention.

FIG. 3 illustrates a bedridden patient exposed to pressure and shear forces when the head of the bed is tilted upwards when no dressing is used (3a), and when a dressing of the invention has been applied to the sacrum region of the patient (3b).

FIG. 7 illustrates the Von Mises stress distribution at the muscle arising from compression and shear in a Finite element (FE) model simulation, when no dressing is used (FIG. 7a), a dressing comprising a gel pad (FIG. 7b), and a dressing according to an exemplary embodiment of the present invention (FIG. 7c).

FIG. 8 illustrates the shear stress distribution at the muscle next to the bones arising from compression and shear in a Finite element (FE) model simulation, when no dressing is used (FIG. 8a), a dressing comprising a gel pad (FIG. 8b), and a dressing according to an exemplary embodiment of the present invention (FIG. 8c).

FIG. 9 illustrates a simulated gel dressing according to an exemplary embodiment of the invention, which dressing has a central pad zone comprising indentations and a lower pad region having a lower gel compressive strength.

FIG. 10 illustrates the mean pressure (hydrostatic stress) distribution at the skin arising from compression in a Finite element (FE) model simulation, when no dressing is used (FIG. 10a), a dressing according to the invention comprising an anisotropic layer in the pad (FIG. 10b) and a dressing according to the present invention comprising an anisotropic layer in the body contact layer (FIG. 10c).

FIG. 11 illustrates the Von Mises stress distribution at the muscle arising from compression in a Finite element (FE) model simulation, when no dressing is used (FIG. 11a), a dressing according to the invention comprising an anisotropic layer in the pad (FIG. 11b) and a dressing according to the present invention comprising an anisotropic layer in the body contact layer (FIG. 11c).

DETAILED DESCRIPTION

The present invention will now be described more fully hereinafter with reference to the accompanying drawings, in which currently preferred embodiments of the present invention are shown. The present invention may, however, be embodied in many different forms and should not be construed as limited to the embodiments set forth herein; rather, these embodiments are provided for thoroughness and completeness, and fully convey the scope of the present invention to the skilled person.

Figure 1A:
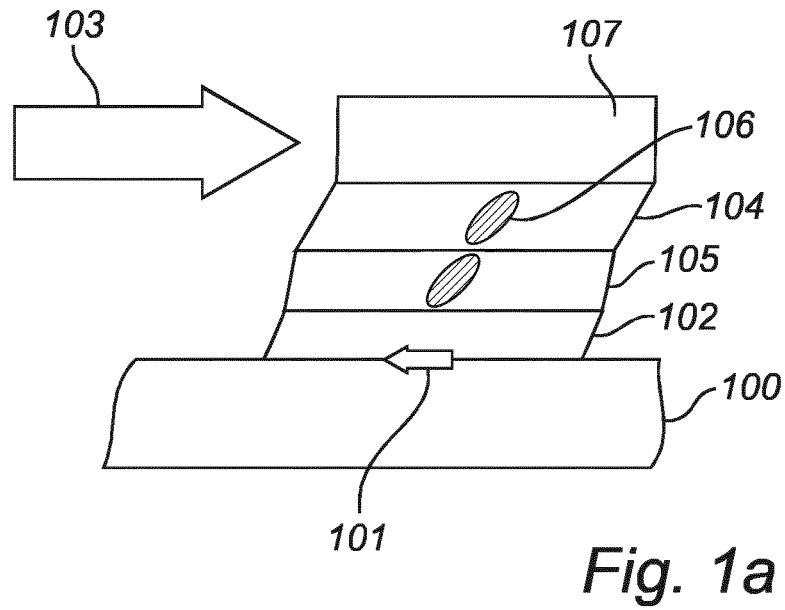
FIGS. 1a and 1b schematically illustrate how pressure, shear and friction contribute to the development of pressure ulcers.
Figure 1B:
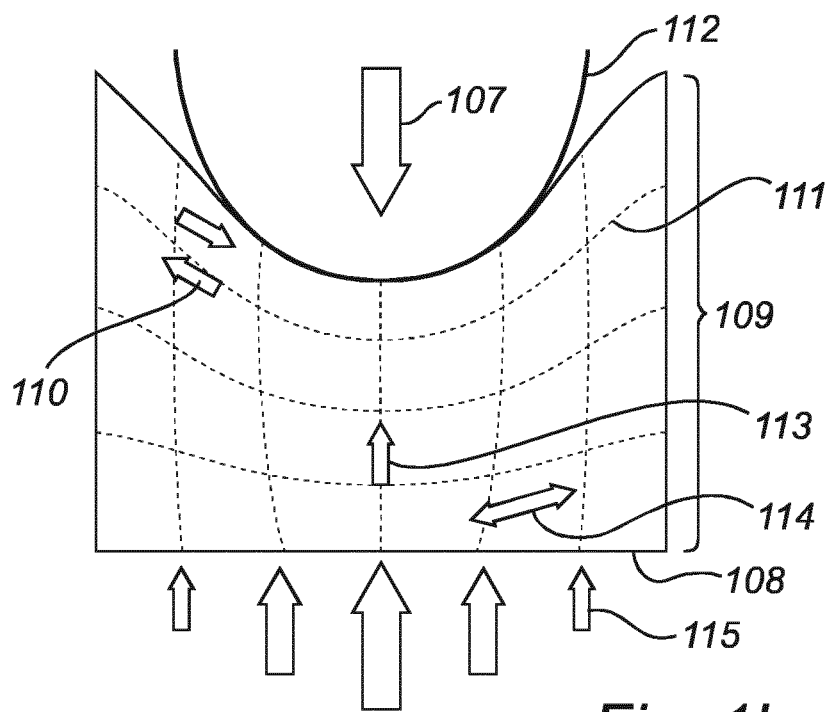

FIGS. 1a and 1b conceptually illustrate how pressure, shear and friction contribute to pressure ulcer development.

When a patient in contact with a support surface 100 moves, friction 101 between the skin 102 and the support surface 100 tends to hold the skin 102 in place and a shear force 103 occurs that displaces and deforms the deeper tissues (muscle 104 and adipose tissue 105). The deeper tissue layers 104 and 105 are typically subject to the worst effect of shear since these layers, in closer proximity to the bone 107, cannot move in a manner like the skin layer 102 does. Instead these layers are stretched but still "stuck". Furthermore, blood vessels 106 may be distorted and compressed (FIG. 1a). Compression of blood vessels 106 by pressure and/or shear may reduce the blood flow to tissues. This may result in tissue hypoxia, build-up of metabolic waste products and, eventually, tissue damage.

Referring to FIG. 1b, when a force 107 is applied perpendicular to the surface of the skin, pressure is exerted onto the skin 108 and subcutaneous tissues 109. Pressure 107 typically compresses the tissues 109 and may distort or deform the skin and the soft tissues (e.g. subcutaneous fat and muscle). Shear 110 may also occur in and between layers 111 of deeper tissues as a result of tissue deformation caused by pressure over a bony prominence 112. Muscle is particularly prone to damage by shear. Compression stresses 113 occur in the axis perpendicular to the direction of the muscle fibers, and tensile stresses 114 occur when the tissue is stretched and deformed along the fiber direction. The arrows 115 represent surface pressure. Deformation of soft tissues is greater when pressure is applied over a bony prominence 112. Damage thus often occurs initially in the soft tissue, i.e. at the muscle/bone interface, and skin breakdown and pressure sore formation occurs later in the process. Hence, when assessing a pressure sore, the full extent of the damage may not be clear or visible.

Referring to FIG. 2a, a medical dressing 200 according to an exemplary embodiment is illustrated. The dressing 200 comprises a backing layer 201, an adhesive body contact layer 202 and a gel pad 203 arranged between the backing layer 201 and the body contact layer 202, wherein the backing layer 201 and the body contact layer 202 extend beyond the periphery of the gel pad 203 to define a border portion 204 around the contour of the pad 203, wherein the dressing 200 further comprises an anisotropic layer 205 having a first (x) direction and a second (y) direction being perpendicular to the first (x) direction; the anisotropic layer 205 being stiffer in the second (y) direction than in first (x) direction.

As used herein, the term "stiffer" means that the anisotropic layer has a higher tensile force at 15% strain in the second (y) direction than in the first (x) direction, as measured according to the tensile test described hereinafter.

As used herein, the term "anisotropic layer" means a layer that has anisotropic stiffness properties; i.e. the stiffness or stretchability is different in the lateral (x) and second (y) directions of the layer. In the present invention, the "anisotropic layer" is stiffer in the second (y) direction and more stretchable in the first (x) direction. The second direction (y) is normally applied along the length of the patient, and may also be referred to as the longitudinal direction (y). The first direction (x) may thus be referred to as the lateral (x) direction.

As used herein, the term "body contact layer" means the layer that is in contact with the skin of a wearer. In the field of medical dressings, in particular, wound dressings, an adhesive film or layer for adhering to the patient is often referred to as a wound contact layer. The present invention is primarily intended for pressure ulcer prevention, i.e. for use on a human body area which is not necessarily in need of wound treatment. Therefore, in this application the adhesive film or layer will be referred to as a body contact layer. However, it should be understood that although the primary use of the invention is pressure ulcer prevention, if nursing personnel decides to use it as a wound dressing, the body contact layer could be applied onto a wound or a scar. The body contact layer preferably is or comprises an adhesive.

The anisotropic layer 205 affects the stiffness of the entire dressing. As illustrated by the arrows in FIG. 2d, the dressing 200 is stiffer in the second (y) direction and more stretchable in the first (x) direction.

The anisotropic layer may be arranged in various ways in the dressing of the present invention.

For example, the anisotropic layer may be arranged between the gel pad and the backing layer.

The anisotropic dressing may be arranged to contact the backing layer and the underlying gel pad. Alternatively, the dressing may comprise a second gel pad arranged on top of the first gel pad; i.e. the anisotropic layer may be arranged between a first and a second gel pad.

Alternatively, as illustrated in FIG. 2a, the anisotropic layer 205 may be arranged between the gel pad 203 and the body contact layer 202.

The inventors have found that anisotropy in close proximity of the skin is advantageous for protecting the skin and underlying soft tissues from shear and compression forces.

In FIGS. 2b and 2c, an alternative arrangement is illustrated. In this embodiment, the anisotropic layer 205 is integrated in the body contact layer 202.

The body contact layer may comprise an adhesive skin-facing layer and an anisotropic layer.

In embodiments, the body contact layer 202 comprises an anisotropic layer 205, a plastic film 206 and a skin-facing layer 207 comprising a silicone adhesive.

The anisotropic layer 205 may be arranged between the plastic film 206 and the skin facing layer 207.

Alternatively, as illustrated in FIG. 2c, the plastic film 206 may be arranged between the anisotropic layer 205 and the skin facing layer 207.

The body contact layer 202 may be perforated or non-perforated. In the embodiment illustrated in FIG. 2c, apertures 208 extend through all the layers of the body contact layer 202. In embodiments, the apertures extend through two of the layers of the body contact layer 202, for example the plastic film 206 and the skin-facing layer 207. The apertures improve the absorption of body fluids into the dressing without compromising the adhesiveness to the skin area.

The incorporation of an anisotropic layer 205 into the body contact layer, regardless of position (on top of the plastic film layer 206 or between the plastic film layer 206 and the skin facing layer 207) is advantageous in terms of reducing shear and compression forces at the skin and in the soft tissues beneath the dressing. This reduces and/or mitigates the risk of developing pressure ulcers. The integration of the anisotropic layer 205 into the body contact layer 202 also provides rigidity to a thin and "flimsy" border portion. The anisotropic layer 202 enhances the integrity of the border of the dressing, and facilitates skin inspection.

In embodiments, the adhesive body contact layer 202 of the dressing covers at least 60% of the surface of the pad 203. Suitably, the adhesive body contact layer 202 covers at least 75% of the surface of the pad.

It is beneficial to have an even distribution of adhesive over the surface of the pad in order to keep the dressing in place during use. Also, a greater coverage of adhesive on the surface of the pad aids in preventing undesirable friction forces which could form between the skin and the dressing as a patient slides in bed.

The body contact layer 202 preferably comprises a silicone based adhesive. Such an adhesive is skin-friendly, and sufficiently adherent to skin such that the dressing stays in place, and maintains its adherence with repeated removal and re-application. The adhesive is easy to remove without causing trauma.

Examples of suitable silicone gels include the two component RTV systems, such as Q72218 (Dow Corning), and SilGel 612 (Wacker Chemie AG) mentioned herein, as well as NuSil silicone elastomers. In embodiments of the invention the adhesive may comprise a soft silicone gel having a softness (penetration) of from 8 to 22 mm, e.g. from 12 to 17 mm, as measured by a method based on ASTM D 937 and DIN 51580, the method being described in European Patent Application No. 14194054.4. The thickness of the adhesive layer is preferably at least 20 μm.

In exemplary embodiments, the adhesive body contact layer 202 comprises a plastic film 206 covered by an adhesive layer 207. The film onto which the adhesive layer is applied may be comprised of a thin plastic film, or a laminate comprising a thin plastic film, e.g. a thin polyurethane film having a thickness from 15 and 100 μm, e.g. from 20 to 80 μm, preferably from 45 to 60 μm.

In alternative embodiments, the body contact layer 202 comprises an adhesive skin-facing layer and an anisotropic layer 205.

The body contact layer 202 is typically co-extensive with the backing layer 201, and has the same outer dimensions.

The border portion 204 forms a closed path around the contour of the pad 203 and the backing layer 201 and body contact layer 202 are bonded to each other in those areas of both layers that extend beyond the periphery of the pad. The adhesive may be a thin acrylic adhesive.

In order to achieve sufficient adhesion properties, the border portion 204 may have a width of 5 to 50 mm and extend along the contour of the pad 203. A smaller sized dressing may have a smaller border portion than a larger sized dressing. Preferably the border portion has a width of 10 to 25 mm and extends along the contour of the pad. This allows for easy handling and application of the product while still maintaining sufficient adhesion upon application.

The backing layer 201 of the dressing may be a thin film, sheet or membrane that is vapour permeable and waterproof. Examples of suitable materials for the backing layer include, but are not limited to polyurethane, polyethylene or polyamide films, silicone films, polyester based nonwoven materials, and laminates of polyester-based nonwoven materials and polyurethane films. Suitably, the backing layer is a polyurethane film having a thickness of from 5 to 40 μm, e.g. from 15 to 25 μm. The backing layer 201 may be partly or fully bonded to the pad 203, for example, via an adhesive such as a pressure sensitive adhesive (e.g. an acrylic adhesive).

Preferably, the backing layer 201 is substantially transparent.

In embodiments, the anisotropic layer 205 has a tensile force at 15% strain of at least 4 N, preferably at least 10 N in the second (y) direction, most preferably at least 15 N, as measured by the tensile test described in the Example section.

The anisotropic layer 205 may be selected from a variety of materials such as nonwovens, films, textile materials, polymeric net materials as long as they exhibit the desired anisotropic stiffness properties. The anisotropic layer 205 may comprise a plurality of reinforcement fibres or filaments extending in the longitudinal direction. The reinforcement fibres or filaments provide the layer with high tensile force in the longitudinal (y) direction. Films or nets made of e.g. polyethylene, polypropylene, polyester, polyurethane or silicone can be used as long as these materials have sufficient strength in the longitudinal direction (y) and sufficient anisotropic properties.

In embodiments, the anisotropic layer 205 comprises a nonwoven. Suitable nonwovens for use as the anisotropic layer are meltblown, spunbond, spunlaced or carded nonwoven webs.

In exemplary embodiments, the anisotropic layer is an oriented fibrous nonwoven layer having more than 50% of the fibres oriented in the longitudinal (y) direction. In this manner, the fibres oriented in the longitudinal (y) direction will provide reinforcement in this direction.

Examples of suitable polymers for use in the nonwoven are polyethylene, polyesters, polypropylene and other polyolefin homopolymers and copolymers. For example, nonwoven webs comprising thermoplastic fibres of polypropylene and polyethylene fibres or mixtures thereof may be used. The webs may have a high content of thermoplastic fibres and contain at least 50%, e.g. at least 70% thermoplastic fibres. The nonwoven may be a mixture of polyethylene and viscose, e.g. in a 70:30 ratio. Natural fibres, for example cotton may also be used as long as they provide the desired properties. The basis weight of the nonwoven may be in the range of from 10 to 80 g/m2, e.g. of from 13 to 50 g/m2. The anisotropic layer may also be a spunbond-meltblown or spunbond-meltblown-spunbond (SMS) web.

In embodiments where the dressing is substantially transparent, the anisotropic layer 205 is preferably also substantially transparent such that it does not obstruct the transparency of the gel dressing.

The anisotropic layer may comprise additives to achieve the desired transparency/opacity. In embodiments, said additive(s) may be selected from the group consisting of dyes, coloring agents or whitening agents.

In embodiments, the anisotropic layer 205 has a tensile force at 15% strain in the second (y) direction that is at least 6 times higher, preferably at least 10 times higher than in the first (x) direction, as measured by the tensile test described herein.

Accordingly, the stay-on ability of the dressing on the skin is enhanced, and the skin and underlying tissue is prevented from becoming "over constrained" which could otherwise be the case when the dressing is stiff in both the first (x) direction and the second (y) direction.

For example, the tensile force at 15% strain may be less than 3 N, preferably less than 1.5 N in the first (x) direction, as measured by the tensile test described herein.

The effect of the anisotropic layer may be explained with reference to FIG. 3.

FIG. 3 illustrates a patient 301 positioned in an adjustable bed 302, where the head of the bed has been elevated and the patient 301 has been placed in a more upright condition. When no dressing is used (FIG. 3a), the patient 301 is subject to pressure compressing the tissue, and to shear forces 303 distorting or deforming the soft tissue layers 304. The individual tissue cells 305 are thus subject to both pressure and compression, and also to shear forces 303 that arise from the patient 301 sliding in bed 302. This has a negative impact on the soft tissue, and the tissue cells 305 are more prone to deformation, which ultimately may lead to the formation of a pressure ulcer.

In FIG. 3b, a dressing 300 according to the present invention has been applied to the sacrum region of the patient 301 such that the stiff, second (y) direction corresponds to the direction of which the tissue is exposed to most shear and stretch (i.e. the sliding direction of a patient). When a dressing is applied to the sacrum region, the pressure forces are reduced by the dressing 300 and distributed over a larger area. This leads to pressure re-distribution and reduced magnitude of critical forces on the skin and underlying tissues. The shear forces 303 are reduced by the dressing 300 since the dressing is stiff in the direction in which the patient 301 slides in bed 302. Therefore, the stiff dressing 300 "locks" the skin and underlying tissues such that they do not stretch excessively in the region where the dressing 300 is applied. The fact that the dressing is flexible in the first (x) direction is advantageous since it prevents the tissues from becoming "over constrained". Instead, the sacral buttocks can spread gently and naturally.

The individual tissue cells 305 in the sacral region of the patient 301 are therefore maintained relatively intact. The stretching of the skin may still occur at skin areas outside the dressing (which areas are at less risk for pressure ulcer formation caused by deformation, pressure and shear). This way, pressure forces, shear forces and the stress and stretch on skin cells and the underlying tissue cells are minimized In embodiments, the gel pad and the dressing are substantially transparent.

As used herein, the term "substantially transparent" means that the dressing should be sufficiently transparent to allow visual inspection of the skin; i.a. to monitor potential skin colour changes or ulcer formation without having to remove the dressing from the skin.

Suitably, the gel pad has an opacity of less than 25%, preferably less than 15% as measured by the opacity test described herein.

The opacity of the gel pad reflects the degree of "untransparency" of the gel. When the gel pad has an opacity of 0%, the gel is completely transparent. If the gel pad has an opacity of 100%, the gel pad has no transparency; i.e. no light can be transmitted through the material. The opacity of the gel pad shows the degree on how clearly the skin can be seen through the gel pad. When the opacity is less than 25%, any shift in color or skin appearance can be observed through the dressing. The opacity is measured in according to the standard method ASTM D2244-11 as described in the Example section.

The assessment for potential tissue damage includes an observation of the skin for changes in color compared with the surrounding skin. The transparency of the dressing of the present invention enables visual inspection of the skin beneath the dressing, and any changes in appearances of the skin may be monitored and recorded.

The gel pad suitably comprises a soft and compliable gel. If the gel is too rigid, this may inflict additional shear forces on the skin.

Hence, in embodiments, the gel has a compressive strength of from 1 to 30 kPa, preferably of from 1 to 15 kPa at a strain of 25%, as measured according to the compression test described herein.

As used herein, the term "compressive strength" refers to the amount of stress required to deform the material at a certain strain. Compressive strength is calculated by dividing the load by the original cross-sectional area of a specimen. The compressive strength as defined here is independent of the maximum compressive strength before fracture (i.e. the maximal stress that a material can take in before it breaks). The compressive strength is measured as described in the Example section.

In embodiments, the gel has a compressive strength of from 5 to 70 kPa, preferably of from 5 to 50 kPa at a strain of 50%, as measured according to the compression test described herein.

This compressive behavior is advantageous for the purpose of preventing pressure ulcers. The gel dressing of the present invention allows for compression at high loads. The low compressive strength of the gel at higher strains (50%) prevents deformation (resulting from compression) to be transferred to the underlying skin and soft tissue. Instead deformation due to high loads is taking place within the dressing.

In embodiments, the gel has a compressive strength of from 2 to 12 kPa, preferably of from 2 to 8 kPa at a strain of 25%, as measured according to the compression test described herein.

A pad with a gel having a compressive strength in that range provides improved soft tissue mimicking and prevention of soft tissue damage. If the gel is too soft, the product may lose efficiency and either break or flatten out in critical areas.

In embodiments of the present invention, the gel as described herein has a water content of less than 15% by weight, preferably less than 10% by weight, further preferably less than 5% by weight. In embodiments, the gel has a water content of from 0.5% by weight to 15% by weight, preferably from 1% by weight to 13% by weight, further preferably from 3% by weight to 12% by weight.

It is believed that conventional hydrogels; i.e. gels containing a significant amount of water as described in the art generally are not suitable to be used as gels in accordance with the present invention.

The composition of the gel as described above enables the dressing to be stored in ambient conditions without requiring special packaging (such as aluminum, hermetically sealed packages etc.), and without compromising the properties of the gel and the dressing. If the water content of the gel is too high, the gel may dry out when stored in ambient conditions. As a result, the gel may become stiffer and harder. Instead, standard packaging may be used and ethylene oxide (EtO) sterilization can be used to sterilize the product.

The gel according to the present invention may be manufactured by polymerizing:
- 15-50% by weight of a hydrophilic acrylic monomer,
- 50-85% by weight of a hydrophilic softening agent,
- 0.001-0.5% by weight of a crosslinker,
- 0.05-0.5% by weight of a polymerization initiator.

The hydrophilic acrylic monomer(s) is (are) preferably selected from monomers yielding a homopolymer with a low glass transition temperature, Tg, such as less than $-10°$ Celsius, preferably less than $-20°$ Celsius.

In embodiments, the hydrophilic acrylic monomer is selected from 4-hydroxybutyl acrylate, methoxy polyethylene glycol acrylate, 2-hydroxyethyl acrylate, hydroxypropyl acrylate or combinations thereof.

The monomer(s) is/are chosen so that the formed co-polymer is hydrophilic, soft, elastic and compatible with the softening agent. The monomers are preferably present in an amount of 15-50% by weight, suitably of 20-35% by weight of the total mixture.

In embodiments, the polymerization mixture further comprises 0.1 to 5% of a monomer containing acidic groups or salts thereof. For example, acrylic acid or, more preferably, 2-acrylamido-2-methylpropane sulfonic acid (AMPS) or salts thereof are used. The monomers containing acidic groups or its salts may enhance the absorption capacity of the gel.

Suitably, a low amount of monomers containing acidic groups or its salts, e.g. 2-acrylamido-2-methylpropane sulfonic acid sodium salt (Na-AMPS) is used, such as from 0.1 to 5% by weight, e.g. from 0.1 to 3% by weight, e.g. from 0.1 to 2% by weight. Acrylic acid and AMPS typically yield homopolymers having a higher glass transition temperature, Tg. Hence, if present in too high amounts, the resulting gel will be too hard.

The hydrophilic softening agent may be selected from polyethylene glycol, glycerol and/or urea or combinations thereof. The total amount of softening agent is 50-85% by weight, suitably 65-80% by weight.

The crosslinker is preferably selected from difunctional acrylates, such as polyethylene glycol diacrylate. A small amount, such as from 0.001 to 0.5% by weight is preferably used, further preferably from 0.001 to 0.2% by weight. A low cross-linking degree is desirable to maintain the softness of the gel.

A polymerization initiator may be an UV initiator selected from 1-hydroxycyclohexyl-phenyl ketone, 2-Hydroxy-2-methylpropiophenone and combinations thereof. The UV initiator allows the gel to be curable in an UV curing process.

The thickness of the gel pad may vary depending on where the dressing is to be applied. Dressings are available in a variety of sizes and shapes suitable for different anatomical locations. Different anatomical sites vary in skin properties, shape of underlying bony prominence, and thickness and types of subcutaneous tissue present. For example, a heel dressing may be thicker than a dressing applied to the sacrum or the face or head of a patient.

In embodiments, the thickness of the gel pad is in the range of from 2 to 10, e.g. from 2 to 6 mm, suitably from 2 to 4 mm. A gel pad that is too thick may cause increased stresses in the soft tissue.

Figure 4:
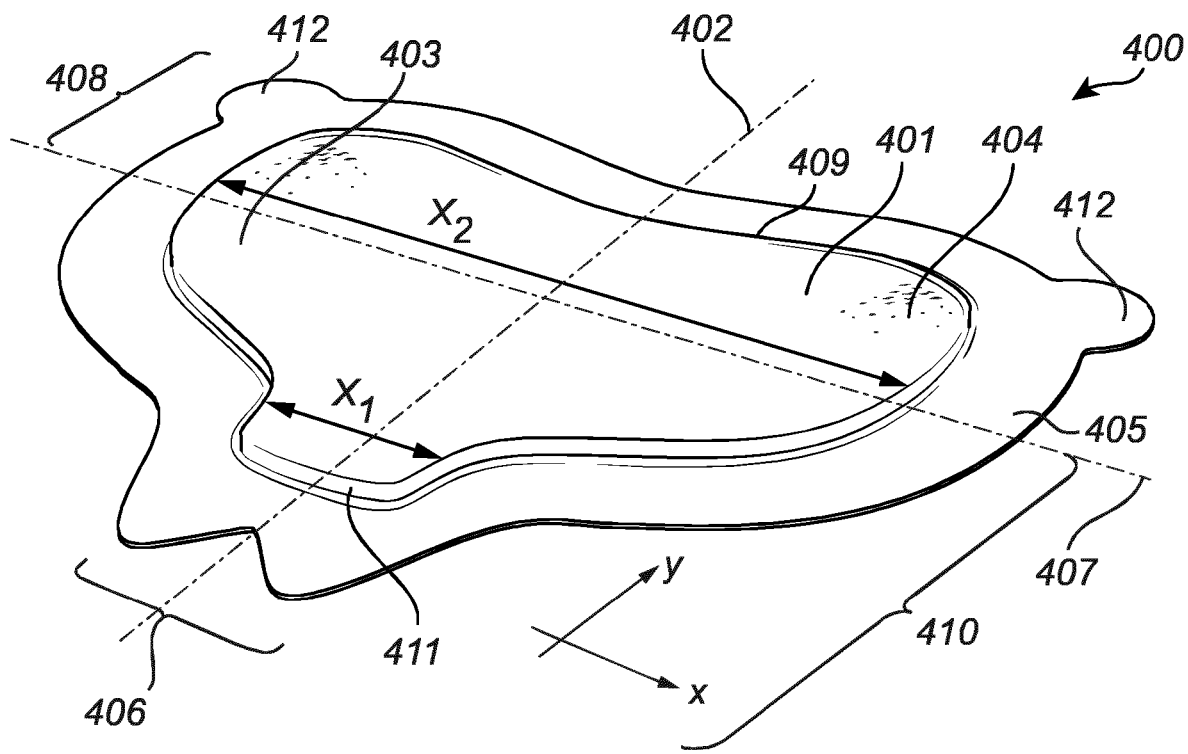
FIG. 4 illustrates a medical dressing according to one exemplary embodiment of the invention.

An exemplary embodiment of the invention is illustrated in FIG. 4. The shape of the dressing is suitable for application to the sacrum area of a patient.

The medical dressing 400 illustrated in FIG. 4 has a lateral (x) extension and a longitudinal (y) extension; the pad 401 being symmetric about a longitudinal center line 402 and the dressing comprising a first lobed portion 403 on one side of the longitudinal center line 402 and a second lobed portion 404 on the other side of the longitudinal center line 402.

The anisotropic layer (not shown) is arranged such that the first (x) direction of the anisotropic layer corresponds to the lateral (x) extension of the dressing 400, and the second (y) direction of the anisotropic layer corresponds to the longitudinal extension of the dressing 400. Hence, the dressing is stiffer in the second (y) direction than in the first (x) direction.

The border portion 405 may be substantially heart shaped such that the first 403 and second 404 lobed portions form part of the lobed upper sides of a heart shape. Suitably, the first and second lobed portions are separated by a forked portion 406 which replaces the pointed lower part of a heart shape. The forked portion 406 comprises a protrusion on either side of an interstice located coaxially with the longitudinal center line.

The shape of the medical dressing 400 is adapted to fit to the sacral region of a human body. The forked portion 406 allows for an improved stay-on ability in the gluteal cleft region. It is important that the dressing remains adhered in this region since otherwise body fluids (for example as a result of incontinence) may enter into the dressing and impair the adhesion to the skin.

The coccyx is an area exposed to a large amount of pressure and shear. It is therefore important to protect this part of the body, and the dressing suitably has a shape that allows for such protection.

Hence, the pad 401 may be divided by a lateral center line 407 into an upper pad region 408 having an upper lateral edge 409 and a lower pad region 410 having a lower lateral edge 411. The width, $x_1$, of the lower lateral edge 411 is between 10 and 40% of the maximum width, $x_2$, of the pad 401 in the lateral (x) direction.

The maximum width, $x_2$, of the pad of the dressing 400 is typically in the range of from 12-30 cm, preferably from 15-20 cm. The width, $x_1$, of the lower lateral edge may be in the range of from 1 to 7 cm, e.g. from 2 to 4 cm, depending on the size of the dressing.

In embodiments, the dressing 400 comprises at least one gripping tab 412; the gripping tab 412 preferably being coplanar with and projecting outwardly from the periphery of the dressing 400.

The gripping tab 412 guides the caregiver to lift the dressing, inspect the skin underneath the dressing, and to thereafter re-apply the dressing onto the skin (in case the skin looks ok). Inspection of skin may still be required, albeit on a less frequent basis when the dressing is transparent. Since the inspection of the skin typically takes place where the patient is lying on the side in the bed, it is beneficial to have at least two gripping tabs such that the caregiver can lift the dressing regardless of which side the patient lies. In FIG. 4, the gripping tab 412 is coplanar with and projects outwardly from the border portion of one of the lobed portions 403 and 404.

Figure 5:
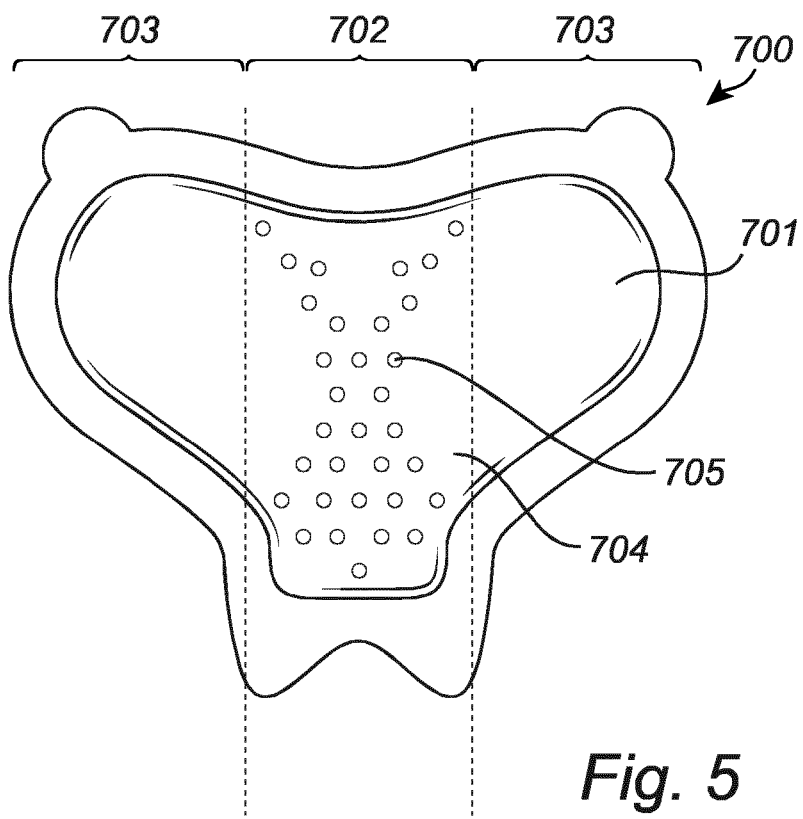
FIG. 5 illustrates an exemplary embodiment of the dressing according to the invention comprising three lateral zones, wherein the central zone comprises indentations.

As illustrated in FIG. 5, the pad 501 may be divided into three separate zones along the longitudinal (y) extension of the dressing 500: one central zone 502 and two lateral zones 503.

The central zone 502 of the dressing 500 is the area exposed to most pressure and shear stresses, especially in the lower part 504 of the central zone 502 which is arranged to cover the coccyx region of a patient. In the embodiment envisioned in FIG. 7, the gel pad comprises a plurality of indentations 505 in at least the central zone 502.

As used herein, the term "indentations" means areas of reduced pad thickness. The indentations may be apertures that extend through the gel pad.

The indentations 505 allow for a localized softening of the gel while preserving the overall properties of the gel dressing. The inventors have found that the skin and the soft tissue underneath is better protected by the provision of indentations 505 in the central zone.

In embodiments, the pad 501 may be divided into three separate zones along the longitudinal (y) extension of the dressing 500: one central zone 502 and two lateral zones 503, wherein the compressive strength of the gel in the central zone 502 is lower than in the lateral zones.

Accordingly, the dressing may be formed of different regions having different properties; i.e. compressive strengths. The inventors have found that the central zone 502 may be softer, i.e. have a lower compressive strength to prevent the soft tissue cells from becoming deformed and damaged. In embodiments, the central dressing zone 502 may have a compressive strength in the range specified above, and the lateral zones 503 of the dressing may have a higher compressive strength.

In another aspect, the invention relates to a dressing as described hereinbefore for use in the prevention and/or mitigation of pressure ulcers.

However, although the primary use of the invention is for prevention, such a dressing may also be used in the treatment of pressure ulcers or wounds, especially low exuding wounds.

Although the dressing of the present invention is primarily directed for prophylactic use, it is preferred that the dressing has sufficient absorbency, as shown in the Example section below. A prophylactic dressing is typically able to handle low exuding wounds and body fluids such as sweat, small amounts of blood, and pus.

EXAMPLES

Tensile Force (in Accordance with Standard ASTM D882-12)
  Apparatus: Tensile tester for e.g. MTS insight
  Tensile tester connected to a computer
  Crosshead speed: 50 mm/min
  Grip separation: 100 mm
  Sample preparation: Test specimens are punched from the material. The width of the specimens is 25 mm and the length at least 50 mm longer than the grip separation if possible. It is of importance that the edges of the specimens are even and without break notches. The specimens are conditioned for at least 24 h in 50 percent RH plus or minus 5 percent RH and 23 degrees centigrade plus or minus 2 degrees centigrade before testing.
  Procedure: The tensile tester is calibrated according to the apparatus instructions and set to zero. The sample is then mounted in the clamps and slack and pre-tension should be minimized. The tensile tester is started and the sample is elongated until break or until reaching 100% elongation, the tensile force (load) versus elongation is recorded.

The following results are expressed by the tensile tester/computer:

Strain [%], extension/gage length,
Load at specific strain (e.g. at 15% strain).

Figure 6A:
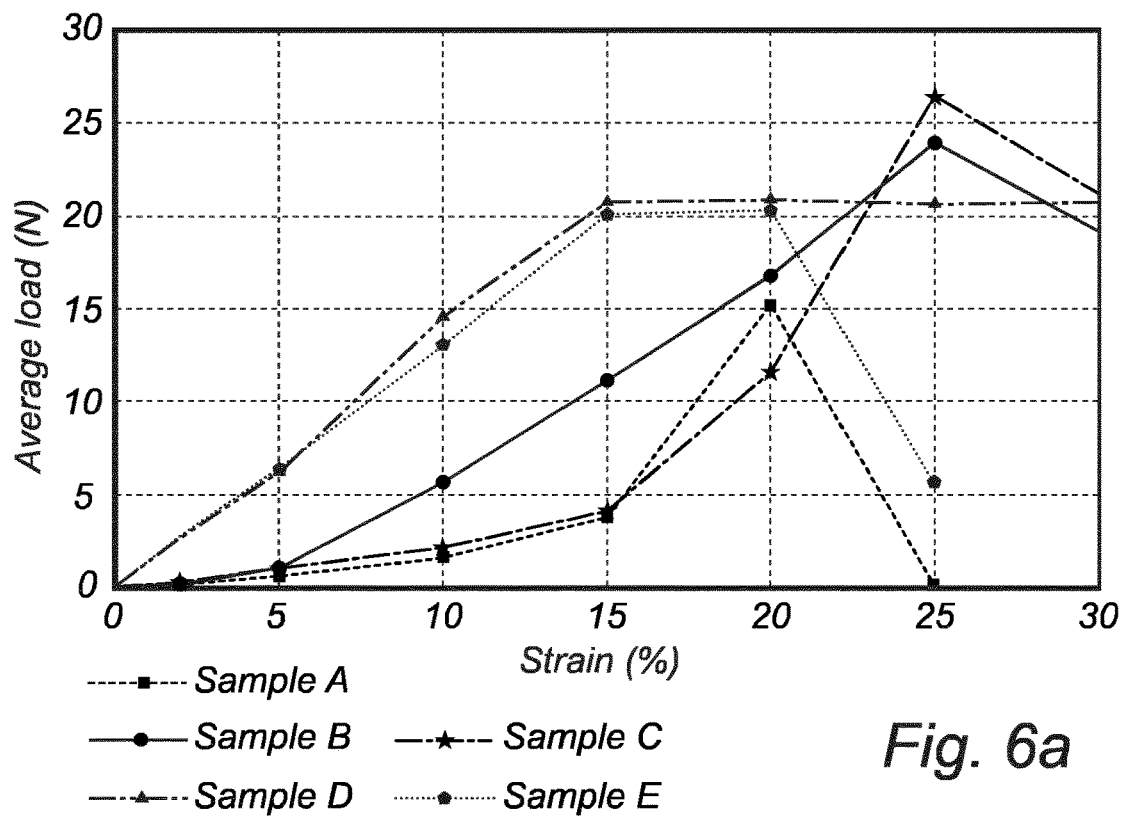
FIG. 6 illustrates the tensile curves for five different types of anisotropic layers in the second (y) direction (FIG. 6a) and in the first (x) direction (FIG. 6b).
Figure 6B:
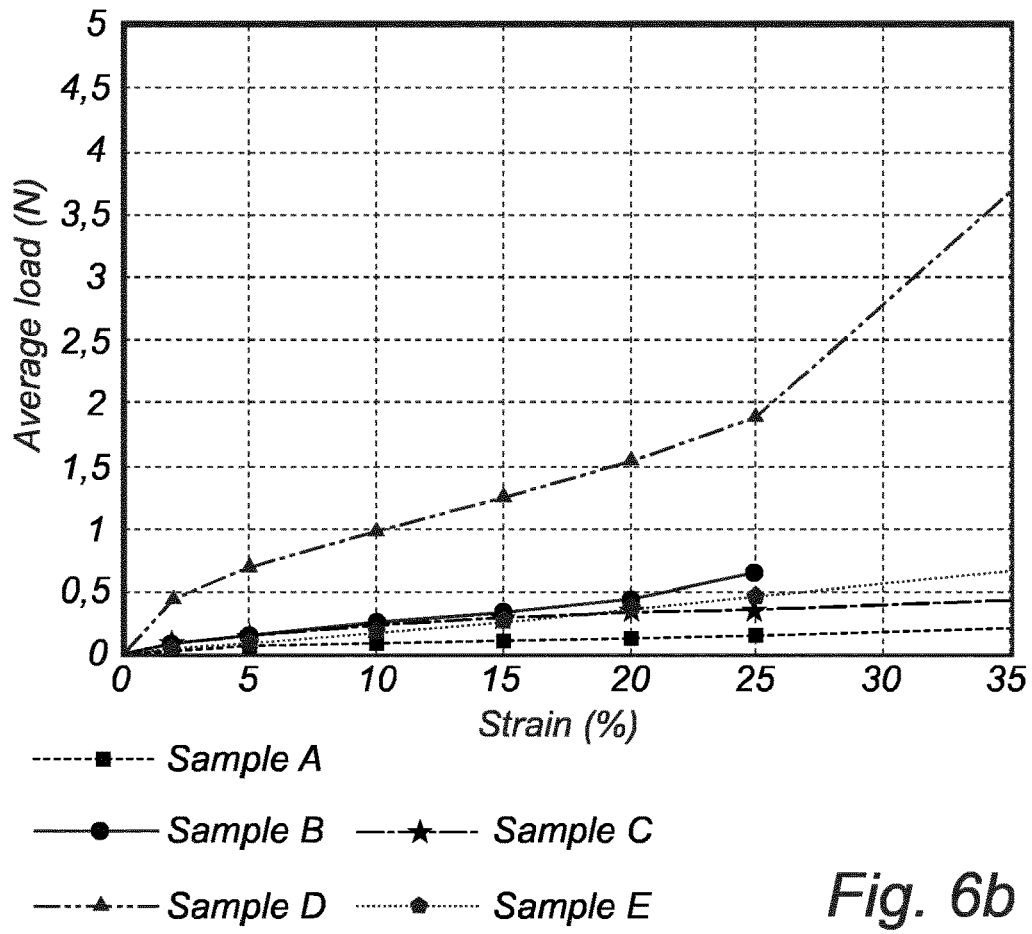
Figure 12:
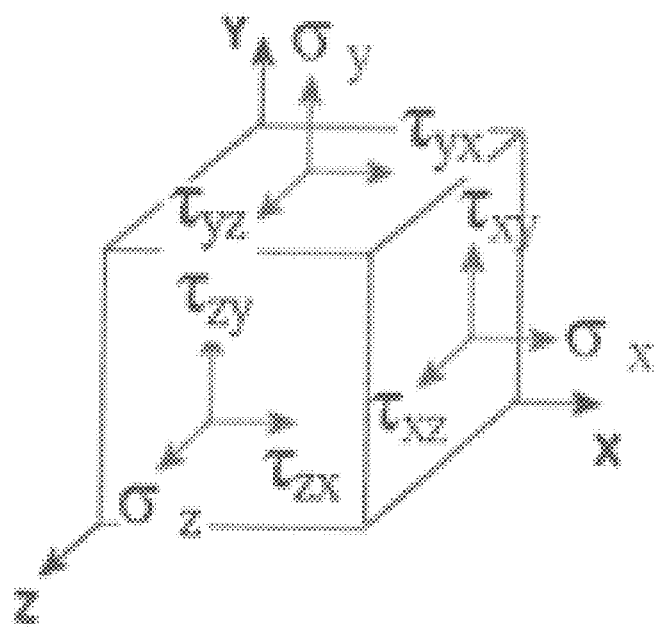
FIG. 12 illustrates the stress components in the Von Mises Stress equation.

Five different anisotropic layers were tested, and their tensile curves are illustrated in FIG. 6. FIG. 6a illustrates the tensile curves in the second (y) direction and FIG. 6b illustrates the tensile curves in the first (x) direction. Sample A was M33116-A (polyamide) from Eschler, sample B was M33116-B (polyamide) from Eschler, sample C was 322223 (polyester) from Eschler, sample D was 114160 Delstar (polyamide sample) from DEKA Medical, and sample E was a 40 gsm spunlace nonwoven comprising viscose and polyethylene (70:30).

Preparation of Gels Suitable for Use in the Inventive Dressing

Gel A 23 g 4-hydroxybutylacrylate, 3 g AMPS, 0.02 g PEG400 diacrylate (from Sartomer), 50 g glycerol, 30 g PEG400 (from Sigma-Aldrich), and 0.15 mg Omnirad 1000 (from IGM Resins) were placed in a speed mixer jar, wherein the UV initiator Omnirad was added last into the mixture. The ingredients were then mixed in the speed mixer for 2 minutes at 2400 rpm.

After mixing, the jars were left to rest for at least 3 hours in a dark box, in order get rid of air bubbles from the gel solution.

Thin gels (up to 5 mm) were then cured for 20 seconds in UV light, for absorption and opacity measurements. Thicker gels (25 mm) were cured for 1 minute in UV light for compression test and analysis of the compressive strength.

The water content of gel A was 9% by weight.

Gel B 29.75 g MPEG450A (from Sigma Aldrich), 0.25 g PEG400diA (from Sartomer), 70 g Glycerol/urea (70/30 mix) and 0.1 Omnirad 1000 (from IGM Resins) were placed in a speed mixer jar, where in the UV initiator Omnirad was added last into the mixture. The ingredients were then mixed in the speed mixer for 2 minutes at 2400 rpm.

After mixing, the jars were left to rest for at least 3 hours in a dark box, in order get rid of air bubbles from the gel solution.

Thin gels (up to 5 mm) were then cured for 20 seconds in UV light, for absorption and opacity measurements. Thicker gels (25 mm) were cured for 1 minute in UV light for compression test and analysis of the compressive strength.

The water content of gel B was 4% by weight.

Absorption Capacity of the Gels

To analyze the absorption capacity on the gels, Solution A (according to EN 13726-1:2002) diluted with distilled water in a ratio of 1:5 was used. The dry weight of the gels was noted. Gels were left to absorb liquid from a wet surface without being plunged into the liquid in room temperature. The surface used was Mesorb®, cut to approximately the same size as the gels (1-2 mm excess material on each side, due to swelling of the gel). The Mesorb® pieces were soaked with 20 ml of liquid (this is how much the piece could retain), and the gel was placed on top of that. A beaker was covered with Parafilm® to prevent evaporation of liquid. After four hours, an additional 10 ml of liquid was added to the Mesorb® piece to make sure it stayed saturated. The setup was then left for another 18 hours. In total, the gels were left to absorb liquid for 22 hours. After the swelling, the weight of the gels was noted again.

Opacity of the Gels (in Accordance with Standard ASTM 2244-11)

After the gels had been wetted and swollen, the opacity was measured with a Minolta Chroma Meter CR 300 according to ASTM D2244-11 to study the opacity after liquid exposure.

The method measures Yxy color space values on specimens that can be used to calculate the opacity number.

Apparatuses: Chroma meter CR-300 and Data processor DP-301.

Sample preparation: The specimen with an initial height of 4 mm is allowed to absorb liquid according to the method described above.

Procedure: Yxy color space values are measured on the wet test specimens. The Chroma meter is calibrated according to the apparatus instructions. The apparatus is set to measure color space values. The specimens are first placed on a black background and the tip of the measuring head is placed flat against the specimen surface. When the measuring head's lamp is light the measuring button is pressed. 5 measurements are taken on each specimen. The specimens are then moved to a white background and the tip of the measuring head is placed flat against the specimen surface. 5 measurements are taken on each specimen.

The following results are measured in the method:
Y x y color space values
Opacity number, $Y_{black}/Y_{white}$ (expressed as %)

Compressive Strength of the Gels (in Accordance with Standard ASTM D3574-11, Test C)

Apparatus: MTS insight
Tensile tester connected to a computer
Crosshead speed: 50 mm/min
Plate distance: 37.5 cm Sample preparation: The area of the specimen should be at least 2500 mm$^2$ (50*50 mm) with a height of at least 20 mm preferably 25 mm. The samples are conditioned for 24 h in 50 percent RH plus or minus 5 percent RH and 23 degrees centigrade plus or minus 2 degrees centigrade before testing.

Procedure: The tensile tester is calibrated according to the apparatus instructions and set to zero. The distance between the upper and lower plate is set to 37.5 mm. The specimen is centered on the supporting plate of the apparatus. The compression foot goes down and the thickness at 140 Pa is determined. The specimen is compressed 50% of this thickness at a speed of 50 mm/min and then the upper plate goes directly back up.

The following results are expressed by the tensile tester/computer:

Load [N]
Specimen thickness at 140 Pa [mm]
Young's modulus at 20% strain and 50% strain [kPa]:

The compressive strength is calculated by dividing the load at specific strains, by the original cross-sectional area of a specimen. The compressive strength as defined here is independent of the maximum compressive strength before fracture (i.e. the maximal stress that a material can take in before it breaks).

The results from absorption, opacity and compressive strength tests for gels suitable for use in the inventive dressing and commercially available gels as used in pads for medical uses are summarized in the table below.

TABLE 1

| Gel mixture | Compressive strength at 50% strain | Compressive strength at 25% strain | Absorption capacity (%) | Opacity (% |
|---|---|---|---|---|
| Gel mixture A | 13.0 | 2.9 | 36.8 | 12.2 |
| Gel mixture B | 15.0 | 2.8 | 84.1 | 9.8 |
| KerraPro ® | 83.5 (45% strain*) | 23.8 | 0 | 29% |
| Elasto-Gel ™ | 64.6 | 14.8 | N/A | N/A |

*Measured at 45% strain since the limit of the load cell (250 N) was reached before 50% strain (since the gel was so stiff).

Finite Element (FE) Modelling

The mechanisms leading to pressure ulcers are not fully understood. Pressure sensing mats can give information on pressure present at the mattress under the skin surface but does not inform on the behaviour inside the soft tissues, at the origin of damage. Therefore, the Finite Element (FE) method offers a great alternative to study the biomechanisms of action for pressure ulcers.

The FE method is a numerical and computational technique used to solve multiphysics problems by solving partial differential equations upon different types of discretizations. The FE method subdivides a large problem or large 3D model into smaller parts called finite elements. The analyses are performed within each elements and the assembly gives a solution to the entire problem.

The workflow for a FE analysis can be explained as follows: creation of a 3D model constituted of finite elements, definition of the material properties of the model, definition of the boundary conditions and loadings to apply to the model according to the problem, computational solving of the problem, and analysis of the results through visualization and calculations.

Finite Element (FE) Settings and Anatomical Model

In order to understand the effect of the dressing according to the present invention, finite Element (FE) models of a pelvis and of a dressing according to the invention were created and analyses were performed to study the effect of pressure and stresses on the skin and in deep tissue layers. The volunteer was a non-smoker healthy adult male of 31 years at the time of the study (year birth 1984, length: 183 cm, weight: 77 kg).

The FE models were prepared in prepared in ANSA 16.0.1 and 17.1.0 (BETA CAE) and the analysis performed in ABAQUS 14.0 (DASSAULT SYSTEM). The FE model of the pelvis was segmented from MRI scans of the pelvis in order to insure the best anatomical accuracy.

The soft tissues were represented as non-linear materials (the muscles were lumped together as one material, the fat and the skin were lumped together as one compressive material), the bones as rigid body. The deformation of the soft tissue caused by compression from the body weight was used to validate the FE model and its material properties with ABAQUS 14.0 (DASSAULT SYSTEM). The validation was carried out by comparing the thickness of the soft tissues before and after compression between the model and the MRI data.

The deformation of the soft tissue was performed by simulating a clinical setting where a patient is lying on a mattress. A soft mattress (30 kPa) was added under the pelvis and the equivalent of the body weight was applied to induce contact and compression of the pelvis on the mattress.

The deformation of the soft tissue due to pure compression was simulated with a vertical displacement of the body on mattress, while the additional effect of the shear force was induced by a following horizontal displacement of the body on the mattress to mimic elevated position.

The following soft tissue layers were investigated for stress distribution, and the following stresses were analysed:

TABLE 2

Soft tissue layers and simulated stresses

| Soft tissue layer | Definition of soft tissue layer | Stresses in compression | Stresses in compression + shear |
|---|---|---|---|
| At the skin | Posterior part of the skin/fat lump | Mean pressure | Mean pressure |
| At the muscle | Posterior part of the muscle, interface between the muscle and the fat | Von Mises stresses, VMS | Von Mises stresses, VMS |
| At the muscle next to the bones | Anterior part of the muscle, focus on the sacrum area, interface between the muscles and the sacrum bones. | | Shear stresses |

"Stresses in compression" means the stresses that arise from compression; i.e. defined as the vertical displacement of the body on a mattress to mimic the compression of the pelvis when the patient is lying horizontally on a mattress.

"Stress in compression+shear" means the stresses that arise from added shear after compression; i.e. defined as the horizontal displacement of the body on a mattress to mimic the sliding of the pelvis after compression when the patient is lying on an inclined mattress.

The mean pressure (or hydrostatic stress) and the Von Mises stresses give an overview of the strain energy density and help to capture the origins of the strains and stresses in the tissues.

"Shear stresses" means stresses in the plane, parallel to the coronal plane or dressing plane, and due to the shear forces that apply to the cross section area parallel to the direction of the force The Von Mises Stresses (VMS) are defined in the Distorsion Energy Theory and represent a common criterion widely used in engineering. The VMS can be defined as:

$$\sigma_{vM} = \sqrt{\frac{1}{2}[(\sigma_{zz}-\sigma_{yy})^2+(\sigma_{yy}-\sigma_{zz})^2+(\sigma_{zz}-\sigma_{zz})^2]+3(\tau_{xy}^2+\tau_{yz}^2+\tau_{zz}^2)}$$

The Mean Pressure (or hydrostatic stress) can be defined as:

$$\sigma Hyd = \tfrac{1}{3}(\sigma xx + \sigma yy + \sigma zz)$$

The strain energy density is separated into different components in order to isolate the hydrostatic stresses and the deviatoric stresses. The deviatoric stresses are represented by the VMS and combine stresses in different directions into an equivalent stress that will take into account normal stresses, shear stresses and distortion. Combined with the hydrostatic stresses, the VMS can give an overview of the separate components of the strain energy density and help to capture the origins of the strains and stresses in the tissues.

The physical and mathematical relationship between force, stress, displacement and strain are the following:

Strain ε is defined as "deformation of a solid due to stress" and can be expressed as:

$$\varepsilon = dl/L_o$$

wherein
dl=change of length or displacement (mm)
$L_o$=initial length (mm)
The Young's modulus E (MPa) is a property of the material and can be defined as:

$$E = \sigma/\varepsilon$$

Shear stresses are stresses parallel to the plane and can be expressed as:

$$T = F_p/A$$

wherein
T=shear stress (MPa)
$F_p$=parallel component force (N)
A=area (mm²)

There are no known values of critical stresses, as it varies between individuals, due to their physiological parameters, health, age and with the duration of exposure to the stresses. Therefore, the evaluation of the effect of the dressings relies on qualitative values. In the FIGS. 9-14, the black areas show higher stresses (critical values of stresses). Critical values of stresses have been defined as high value of stresses showing difference with "no dressing" and the dressings.

The critical value of stresses correspond to about 1 kg for 10 cm2 (around 10 kPa), except for the shear stresses, where a lower value of the critical stresses was used, corresponding to about 100 g for 10 cm2 (around 1 kPa), as the stresses are applied parallel to the muscle fibers and therefore against a more natural compressive behaviour.

Effect of Inventive Dressing

An exemplary dressing in accordance with the invention was created from technical CAD drawings and was designed to match the properties of the dressing as defined in claim 1.

The dressing comprised a gel pad, wherein the compressive strength of the gel at 25% strain was 4.2 kPa, and the Youngs modulus, E, was 0.008 MPa. The dressing further comprised an anisotropic layer. A simulated anisotropic layer in accordance with sample E above was inserted into the dressing concept. The simulated anisotropic layer refers to a shell with properties similar to a layer having a tensile force at 15% strain of 20.6 N in the second (y) direction, and 0.3 N in the first (x) direction. The inventive dressing was compared with a dressing comprising only a gel pad (with the same properties specified above), and with the scenario when no dressing was used.

The rest of the components and properties of the simulated dressings were identical in the simulations; i.e. they had identical shapes, and both comprised a simulated backing layer and a border portion surrounding the gel pad. In the simulations, the skin-facing surface of the dressings was fully adherent to the skin. For all dressings, the gel pad material was considered as linear elastic isotropic material and nearly incompressible.

The material properties of the different dressings were defined by actual laboratory measurements in tension and compression based on ASTM D 882-12 and ASTM D 3574-11.

Simulations were performed to analyse the stresses in compression and in compression+shear. The simulated model was wearing: no dressing, gel dressing (referred to as "gel dressing A") and inventive dressing (referred to as "gel dressing B", respectively.

FIG. 7 illustrates the Von Mises stresses in the soft tissue layers (i.e. at the muscle) when the model has been subject to compression and shear. FIG. 7a illustrates the situation when no dressing is used, FIG. 7b illustrates gel dressing A, FIG. 7c illustrates Inventive gel dressing B.

As can be seen, the critical VMS are completely reduced in the muscle of the sacrum when the inventive dressing is used. It can be concluded that the anisotropic gel dressing B is advantageously used for removing shear and compression stresses in the soft tissue, and has a significant preventative effect when it comes to the formation of pressure ulcers.

As can be observed in FIG. 7b, the gel dressing A substantially reduces the stresses at the muscle (although not comprising any anisotropic layer), which is believed to be due to the softness and low compressive strength of the gel.

The results are also presented in Table 3 below in terms of the ability of the dressings to reduce the volume of tissue under critical stresses, both for a simulated compression setup and for compression+shear (reflecting the results of FIG. 7).

The ability to reduce the volume of tissue under critical stresses is calculated as described hereinbelow, wherein the performance of the dressing is defined as the percentage reduction of volume of tissue under critical stress when compared to no dressing:

$$\text{Reduction (\%)} = \frac{(V_{nd} - V_d)}{V_{nd}} \times 100$$

with Reduction (%)=percentage reduction of volume of tissue under critical stress
with $V_{nd}$=Volume of tissue under critical stress with no dressing
with $V_d$=Volume of tissue under critical stress with dressing

TABLE 3

Percentage reduction of volume of muscle under critical VMS stress

| Critical stress studied in FE | Compression | | Compression + shear | |
|---|---|---|---|---|
| | Gel dressing A compared to no dressing | Gel dressing B compared to no dressing | Gel dressing A compared to no dressing | Gel dressing B compared to no dressing |
| % reduction of volume of muscle under critical VMS stress | 46 | 84 | 77 | 100 |

The shear at the muscle next to the bones was also studied. Shear stresses occur in the tissue in numerous settings, and they are due to shear forces, that have been identified as one of the major causes of pressure ulcers. For the shear stresses, the critical value of stresses correspond to about 100 g for 10 cm2 (around 1 kPa), as the stresses are applied parallel to the muscles fibers and therefore against a more "natural" compressive behavior.

FIG. 8 illustrates the effect of the gel dressings A and B with respect to reducing shear stresses at the muscle next to the bones in the sacrum area.

As illustrated in FIG. 8c, the inventive gel dressing B completely removed the critical shear stresses at the muscles next to the sacral bone (FIG. 8c), and the calculated reduction of volume under critical shear stresses was 100%. This clearly illustrate the effect of the anisotropic dressing of the present invention, when subject to harmful shear forces.

The gel dressing A, as illustrated in FIG. 8b, also had a significant effect on the reduction of critical shear stresses, and this is believed to be due to the low compressive strength of the gel.

Location of the Anisotropic Layer

In the second set of simulations, the impact of location of the anisotropic layer was studied. The general construction of the simulated dressings is illustrated in FIG. 9. The dressing 900 comprised a gel pad 901, wherein the gel had a compressive strength of 4.2 kPa at 25% strain, except for in the coccyx region 902 of the pad, where the compressive strength was 3.1 kPa. Indentations 903 were provided in the central zone of the dressings, and an intermediate, isotropic layer was inserted to the gel (to stabilize for the low compressibility of the gel). Both dressings comprised an anisotropic layer having a tensile force at 15% strain of 20.6 N in the second (y) direction, and 0.3 N in the first (x) direction. The difference between the two gel based dressings was the location of the anisotropic layer: in the middle of the dressing (referred to as Gel dressing C), and in the body contact layer; i.e. in close proximity of the skin (referred to as Gel dressing D).

FIG. 10 illustrates the critical hydrostatic stress (mean pressure) distribution at the skin in the sacrum region after exposure to pressure and compression for the situation when no dressing was used (FIG. 10a), Gel dressing C (FIG. 10b), and Gel dressing D (FIG. 10c). As can be observed, the anisotropic layer reduces the critical compression stresses at the skin (FIGS. 10b and c) compared to when no dressing is used (10a). Surprisingly, this effect is enhanced when the anisotropic layer is incorporated into the body contact layer; i.e. when the anisotropy is localized in close proximity of the skin (FIG. 10c). Nearly all critical hydrostatic stresses are reduced with the inventive dressing D.

The effect was also analysed deeper in the soft tissue; i.e. at the muscle. FIG. 11 illustrates the distribution of critical VMS stresses at the muscle (shown as black spots) when no dressing has been used (FIG. 11a) compared to Gel Dressing C (FIG. 11b) and Gel dressing D (FIG. 11c). As can be seen, the anisotropic layer remarkably reduces the critical VMS stresses in the muscle (FIGS. 11b and c), and the protective effect on soft tissue is further enhanced when the anisotropic layer is arranged close to the skin (in the body contact layer) as illustrated in FIG. 11c.

The effect of the dressing can also be represented as a calculation of the volume of soft tissue (muscle) subject to critical VMS stresses, as illustrated in table 4 below.

TABLE 4

| Percentage reduction of volume of muscle under critical VMS stress | | |
|---|---|---|
| | Gel dressing C compared to no dressing | Gel dressing D compared to no dressing |
| % reduction of volume of muscle under critical VMS stress | 88.2% | 99.2% |

Other embodiments of the invention will be apparent to those skilled in the art from consideration of the specification or practice of the invention disclosed herein. It is intended that the specification and examples be considered as exemplary only, with the true scope of the invention being indicated by the following claims.

The invention claimed is:

1. A medical dressing comprising a backing layer, a body contact layer and a gel pad arranged between the backing layer and the body contact layer, wherein the backing layer and the body contact layer extend beyond a periphery of the gel pad to define a border portion around a contour of the pad, wherein the dressing further comprises an anisotropic layer having a first (x) direction and a second (y) direction being perpendicular to the first (x) direction, wherein the anisotropic layer is stiffer in the second (y) direction than in first (x) direction, and wherein the gel has a compressive strength of from 1 to 30 kPa at a strain of 25%, as measured according to ASTM D3574-11, test C.

2. The medical dressing according to claim 1, wherein the anisotropic layer is arranged between the gel pad and the backing layer.

3. The medical dressing according to claim 1, wherein the anisotropic layer is arranged between the gel pad and the body contact layer.

4. The medical dressing according to claim 1, wherein the anisotropic layer is integral with the body contact layer.

5. The medical dressing according to claim 1, wherein the dressing is substantially transparent.

6. The medical dressing according to claim 1, wherein the gel has a water content of less than 15% by weight.

7. The medical dressing according to claim 1, wherein the medical dressing has a lateral (x) extension and a longitudinal (y) extension: the pad being symmetric about a longitudinal center line and the dressing comprising a first lobed portion on one side of the longitudinal center line and a second lobed portion on the other side of the longitudinal center line.

8. The medical dressing according to claim 7, wherein the anisotropic layer is arranged such that the first (x) direction of the anisotropic layer corresponds to the lateral (x) extension of the dressing, and the second (y) direction of the anisotropic layer corresponds to the longitudinal extension of the dressing.

9. The medical dressing according to claim 8, wherein the medical dressing is divided into three separate zones along the longitudinal (y) extension of the dressing: one central zone and two lateral zones, wherein the gel pad in at least the central zone comprises a plurality of indentations.

10. The medical dressing according to claim 8, wherein the medical dressing is divided into three separate zones along the longitudinal (y) extension of the dressing: one central zone and two lateral zones, wherein the compressive strength of the gel in the central zone is lower than in the lateral zones.

11. The medical dressing according to claim 1, wherein the dressing comprises at least one gripping tab.

12. A method comprising:
a) applying the dressing accordingly to claim 1 to a subject at an area of risk of developing a pressure ulcer, thereby reducing the risk of the development of a pressure ulcer at the area of risk of developing a pressure ulcer.

13. A medical dressing comprising a backing layer, a body contact layer and a gel pad arranged between the backing layer and the body contact layer, wherein the backing layer and the body contact layer extend beyond a periphery of the gel pad to define a border portion around a contour of the pad, wherein the dressing further comprises an anisotropic layer having a first (x) direction and a second (y) direction being perpendicular to the first (x) direction, wherein the anisotropic layer is stiffer in the second (y) direction than in first (x) direction and, wherein the anisotropic layer has a tensile force at 15% strain in the second (y) direction of at least 4 N, as measured by ASTM D882-12.

14. A medical dressing comprising a backing layer, a body contact layer and a gel pad arranged between the backing layer and the body contact layer, wherein the backing layer and the body contact layer extend beyond a periphery of the gel pad to define a border portion around a contour of the pad, wherein the dressing further comprises an anisotropic layer having a first (x) direction and a second (y) direction being perpendicular to the first (x) direction, wherein the anisotropic layer is stiffer in the second (y) direction than in first (x) direction, and wherein the anisotropic layer has a tensile force at 15% strain in the second (y) direction that is at least 6 times higher than in the first (x) direction, as measured by ASTM D882-12.

15. A medical dressing comprising a backing layer, a body contact layer and a gel pad arranged between the backing layer and the body contact layer, wherein the backing layer and the body contact layer extend beyond a periphery of the gel pad to define a border portion around a contour of the pad, wherein the dressing further comprises an anisotropic layer having a first (x) direction and a second (y) direction being perpendicular to the first (x) direction, wherein the anisotropic layer is stiffer in the second (y) direction than in first (x) direction, and wherein the gel pad has an opacity of less than 25% as measured by ASTM 2244-11.

16. A medical dressing comprising a backing layer, a body contact layer and a gel pad arranged between the backing layer and the body contact layer, wherein the backing layer and the body contact layer extend beyond a periphery of the gel pad to define a border portion around a contour of the pad, wherein the dressing further comprises an anisotropic layer having a first (x) direction and a second (y) direction being perpendicular to the first (x) direction, wherein the anisotropic layer is stiffer in the second (y) direction than in first (x) direction, and wherein the gel has a compressive strength of from 5 to 70 kPa at a strain of 50%, as measured according to ASTM D3574-11, test.

\* \* \* \* \*